US009861719B2

(12) United States Patent
Boyer et al.

(10) Patent No.: US 9,861,719 B2
(45) Date of Patent: *Jan. 9, 2018

(54) MICROPOROUS MATERIAL

(71) Applicant: PPG INDUSTRIES OHIO, INC., Cleveland, OH (US)

(72) Inventors: James L. Boyer, Monroeville, PA (US); Christine Gardner, Irwin, PA (US); Carol L. Knox, Monroeville, PA (US); Luciano M. Parrinello, Allison Park, PA (US); Robert Swisher, Pittsburgh, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/045,824

(22) Filed: Oct. 4, 2013

(65) Prior Publication Data

US 2014/0037922 A1 Feb. 6, 2014

Related U.S. Application Data

(63) Continuation-in-part of application No. 13/473,001, filed on May 16, 2012, now abandoned, which is a continuation of application No. 12/761,020, filed on Apr. 15, 2010, now Pat. No. 8,435,631.

(51) Int. Cl.
| | | |
|---|---|---|
| *A61L 9/12* | (2006.01) | |
| *B01D 39/16* | (2006.01) | |
| *A61L 9/04* | (2006.01) | |
| *C08J 9/00* | (2006.01) | |
| *C08J 9/28* | (2006.01) | |
| *C08J 9/36* | (2006.01) | |

(52) U.S. Cl.
CPC ............... *A61L 9/12* (2013.01); *A61L 9/042* (2013.01); *B01D 39/1676* (2013.01); *C08J 9/0066* (2013.01); *C08J 9/28* (2013.01); *C08J 9/365* (2013.01); *A61L 2209/131* (2013.01); *B01D 2239/0471* (2013.01); *C08J 2201/0502* (2013.01); *C08J 2205/044* (2013.01); *C08J 2429/00* (2013.01); *Y10T 428/24942* (2015.01); *Y10T 428/24998* (2015.04); *Y10T 428/249921* (2015.04); *Y10T 428/249978* (2015.04)

(58) Field of Classification Search
CPC ... C08J 9/28; C08J 9/0066; C08J 9/365; C08J 2205/044; C08J 2429/00; C08J 2201/0502
USPC .......................................... 428/315.5, 315.9
See application file for complete search history.

(56) References Cited

U.S. PATENT DOCUMENTS

| | | | |
|---|---|---|---|
| 2,772,322 A | 11/1956 | Witt et al. | |
| 3,351,495 A | 11/1967 | Larsen et al. | |
| 3,696,061 A | 10/1972 | Selsor et al. | |
| 3,862,030 A | 1/1975 | Goldberg | |
| 4,161,283 A | 7/1979 | Hyman | |
| 4,339,079 A | 7/1982 | Sato et al. | |
| 4,793,555 A | 12/1988 | Lee et al. | |
| 4,809,912 A | 3/1989 | Santini | |
| 4,824,707 A | 4/1989 | Spector | |
| 4,889,286 A | 12/1989 | Spector | |
| 4,957,787 A | 9/1990 | Reinhardt et al. | |
| 4,959,208 A | 9/1990 | Chakrabarti et al. | |
| 5,032,450 A | 7/1991 | Rechlicz et al. | |
| 5,035,886 A | 7/1991 | Chakrabarti et al. | |
| 5,196,262 A | 3/1993 | Schwarz et al. | |
| 5,230,837 A | 7/1993 | Babasade | |
| 5,230,867 A | 7/1993 | Kunze et al. | |
| 5,236,963 A | 8/1993 | Jacoby et al. | |
| 5,326,391 A | 7/1994 | Anderson et al. | |
| 5,455,043 A | 10/1995 | Fischel-Ghodsian | |
| 5,875,968 A | 3/1999 | Miller et al. | |
| 6,387,519 B1 | 5/2002 | Anderson et al. | |
| 7,481,380 B2 | 1/2009 | Kvietok et al. | |
| 7,498,369 B2 | 3/2009 | Whear et al. | |
| 7,579,060 B2 | 8/2009 | Sakai et al. | |
| 8,435,631 B2 * | 5/2013 | Boyer et al. ............... | 428/319.3 |
| 2003/0191236 A1 | 10/2003 | Buckmann et al. | |
| 2005/0196601 A1 | 9/2005 | Fitzgerald et al. | |
| 2005/0199742 A1 | 9/2005 | Maat | |
| 2005/0211790 A1 | 9/2005 | Kvietok et al. | |
| 2006/0076429 A1 | 4/2006 | Kvietok et al. | |
| 2006/0097065 A1 | 5/2006 | Kvietok et al. | |
| 2006/0097066 A1 | 5/2006 | Kvietok et al. | |
| 2006/0231641 A1 | 10/2006 | Uchiyama et al. | |
| 2006/0233538 A1 | 10/2006 | Tollens et al. | |
| 2006/0237555 A1 | 10/2006 | Cetti et al. | |
| 2007/0158456 A1 | 7/2007 | Spector | |
| 2008/0191050 A1 | 8/2008 | Blondeau et al. | |
| 2009/0105411 A1 * | 4/2009 | Erdem et al. ................. | 524/591 |
| 2009/0188986 A1 | 7/2009 | Blondeau et al. | |
| 2010/0264232 A1 | 10/2010 | Gruenbacher et al. | |
| 2010/0308126 A1 | 12/2010 | Gruenbacher et al. | |
| 2011/0198837 A1 | 8/2011 | Parrinello et al. | |
| 2011/0256364 A1 | 10/2011 | Boyer et al. | |
| 2012/0018527 A1 | 1/2012 | Duddington et al. | |

FOREIGN PATENT DOCUMENTS

| | | |
|---|---|---|
| CA | 2662806 | 7/2009 |
| CA | 2662816 | 7/2009 |

(Continued)

*Primary Examiner* — Hai Vo
(74) *Attorney, Agent, or Firm* — The Webb Law Firm

(57) ABSTRACT

Microporous materials that include thermoplastic organic polyolefin polymer (e.g., ultrahigh molecular weight polyolefin, such as polyethylene), particulate filler (e.g., precipitated silica), and a network of interconnecting pores, are described. The microporous materials of the present invention possess controlled volatile material transfer properties. The microporous materials can have a density of at least 0.8 g/cm$^3$; and a volatile material transfer rate, from the volatile material contact surface to the vapor release surface of the microporous material, of from 0.04 to 0.6 mg/(hour*cm$^2$). In addition, when volatile material is transferred from the volatile material contact surface to the vapor release surface, the vapor release surface is substantially free of volatile material in liquid form.

16 Claims, No Drawings

(56) References Cited

FOREIGN PATENT DOCUMENTS

| EP | 1118338 A2 | 7/2001 |
|----|------------|--------|
| WO | 97/12518 | 4/1997 |
| WO | 98/16262 | 4/1998 |
| WO | 2006/029252 A1 | 3/2006 |
| WO | 2009024802 A1 | 2/2009 |
| WO | 2010120960 A1 | 10/2010 |
| WO | 2010120961 A2 | 10/2010 |
| WO | 2010121039 A2 | 10/2010 |

* cited by examiner

MICROPOROUS MATERIAL

CROSS-REFERENCE TO RELATED APPLICATIONS

This application is a continuation-in-part application of U.S. patent application Ser. No. 13/473,001 filed May 16, 2012, now abandoned, which is a continuation of U.S. patent application Ser. No. 12/761,020, filed Apr. 15, 2010, now U.S. Pat. No. 8,435,631, both of which are incorporated herein by reference.

JOINT RESEARCH AGREEMENT

The invention claimed herein was made as a result of activities undertaken within the scope of the joint research agreement between The Procter & Gamble Company and PPG Industries, Inc. effective on Sep. 15, 2009.

FIELD OF THE INVENTION

The present invention relates to microporous materials that possess controlled volatile material transfer properties. The microporous material includes thermoplastic organic polymer, particulate filler, and a network of interconnecting pores.

BACKGROUND OF THE INVENTION

The delivery of volatile materials, such as fragrances, e.g., air fresheners, may be achieved by means of a delivery apparatus that includes a reservoir containing volatile material. The delivery apparatus or delivery device typically includes a vapor permeable membrane that covers or encloses the reservoir. Volatile material within the reservoir passes through the vapor permeable membrane and is released into the atmosphere, e.g., air, on the atmospheric side of the membrane. Vapor permeable membranes are typically fabricated from organic polymers and are porous.

The rate at which volatile material passes through the vapor permeable membrane is generally an important factor. For example, if the rate at which volatile material passes through the vapor permeable membrane is too low, properties associated with the volatile material, such as fragrance, will typically be undesirably low or imperceptible. If, on the other hand, the rate at which volatile material passes through the vapor permeable membrane is too high, the reservoir of volatile material may be depleted too quickly, and properties associated with the volatile material, such as fragrance, may be undesirably high or in some instances overpowering.

It is also generally desirable to minimize or prevent the formation of liquid volatile material on the atmospheric or exterior side of the vapor permeable membrane, from which the volatile material is released into the atmosphere, e.g., into the air. Liquid volatile material that passes through the exterior side of the vapor permeable membrane may collect, e.g., puddle, within or on the exterior side of the membrane and leak from the delivery device resulting in, for example, staining of articles, such as clothing or furniture, that come into contact with the liquid volatile material. In addition, the formation of liquid volatile material on the exterior side of the vapor permeable membrane may result in the uneven release of volatile material from the delivery device.

Further increases in ambient temperature may increase the rate at which volatile material passes through the vapor permeable membrane to undesirably high rates. For example, a delivery device that is used within the passenger compartment of an automobile may be exposed to increases in ambient temperature. As such, minimizing the increase in the rate at which volatile material contained within the device passes through the vapor permeable membrane, as a function of increasing ambient temperature, is typically desirable.

It would be desirable to develop new microporous materials that possess controlled volatile material transfer properties. It would be further desirable that when such newly developed microporous materials are used as a vapor permeable membrane in a delivery device, the microporous material minimizes the formation of liquid volatile material on the exterior side or surface of the membrane. In addition, the rate at which volatile material passes through such microporous materials should increase minimally with increases in ambient temperature.

SUMMARY OF THE INVENTION

In accordance with the present invention there is provided, a microporous material comprising:

(a) a matrix of substantially water-insoluble thermoplastic organic polymer comprising polyolefin;

(b) finely divided, substantially water-insoluble particulate filler, said particulate filler being distributed throughout said matrix and constituting from 40 to 90 percent by weight, based on the total weight of said microporous material; and (c) a network of interconnecting pores communicating substantially throughout said microporous material;

wherein said microporous material has
a density of at least 0.8 g/cm$^3$,
a volatile material contact surface,
a vapor release surface, wherein said volatile material contact surface and said vapor release surface are substantially opposed to each other, and
a volatile material transfer rate from said volatile material contact surface to said vapor release surface of from 0.04 to 0.6 mg/(hour*cm$^2$), and
wherein when volatile material is transferred from said volatile material contact surface to said vapor release surface (at a volatile material transfer rate of from 0.04 to 0.6 mg/(hour*cm$^2$)), said vapor release surface is substantially free of volatile material in liquid form.

Further, the present invention provides a microporous material comprising:

(a) a matrix of substantially water-insoluble thermoplastic organic polymer comprising polyolefin;

(b) finely divided, substantially water-insoluble particulate filler, said particulate filler being distributed throughout said matrix and constituting from 40 to 90 percent by weight, based on the total weight of said microporous material; and (c) a network of interconnecting pores communicating substantially throughout said microporous material;

wherein said microporous material has
a density of less than 0.8 g/cm$^3$,
a volatile material contact surface,
a vapor release surface, wherein said volatile material contact surface and said vapor release surface are substantially opposed to each other, wherein (i) at least a portion of said volatile material contact surface has a first coating thereon, and/or (ii) at least a portion of said vapor release surface has a second coating thereon,
a volatile material transfer rate from said volatile material contact surface to said vapor release surface of from 0.04 to 0.6 mg/(hour*cm$^2$), and wherein when volatile material is transferred from said volatile material contact surface to said vapor release surface (at a volatile material transfer rate of from 0.04 to 0.6 mg/(hour*cm$^2$)), said vapor release surface is substantially free of volatile material in liquid form.

Also, the present invention provides, a microporous material comprising:

(a) a matrix of substantially water-insoluble thermoplastic organic polymer comprising polyolefin;

(b) finely divided, substantially water-insoluble particulate filler, said particulate filler being distributed throughout said matrix and constituting from 40 to 90 percent by weight, based on the total weight of said microporous material; and (c) a network of interconnecting pores communicating substantially throughout said microporous material;
wherein said microporous material has,
a volatile material contact surface,
a vapor release surface, wherein said volatile material contact surface and said vapor release surface are substantially opposed to each other, wherein (i) at least a portion of said volatile material contact surface has a first coating thereon, and/or (ii) at least a portion of said vapor release surface has a second coating thereon, wherein said first coating and said second coating are each independently selected from a coating composition comprising poly(vinyl alcohol), and
a volatile material transfer rate, from said volatile material contact surface to said vapor release surface, of at least 0.04 mg/(hour*cm$^2$), and
wherein when said microporous material, i.e., the poly (vinyl alcohol coated microporous material, is exposed to a temperature increase of from 25° C. to 60° C., said volatile material transfer rate increases by less than or equal to 150 percent.

DETAILED DESCRIPTION OF THE INVENTION

As used herein and in the claims, the term "volatile material contact surface" means that surface of the microporous material that faces and, typically, is in contact with the volatile material, which is, for example, contained in a reservoir, as described in further detail below.

As used herein and in the claims, the term "vapor release surface" means that surface of the microporous material that does not face and/or contact directly the volatile material, and from which surface volatile material is released into an exterior atmosphere in a gaseous or vapor form.

As used herein and in the claims, the term "(meth) acrylate" and similar terms, such as "esters of (meth)acrylic acid", means acrylates and/or methacrylates.

As used herein and in the claims, the "volatile material transfer rate" of the microporous materials was determined in accordance with the following description. A test reservoir, having an interior volume sufficient to contain 2 milliliters of volatile material, such as benzyl acetate, was fabricated from a clear thermoplastic polymer. The interior dimensions of the reservoir was defined by a circular diameter at the edge of the open face of approximately 4 centimeters and a depth of no greater than 1 centimeter. The open face was used to determine the volatile material transfer rate. With the test reservoir laying flat (with the open face facing upward), about 2 milliliters of benzyl acetate was introduced into the test reservoir. With benzyl acetate introduced into the test reservoir, a sheet of microporous material having a thickness of from 6 to 18 mils was placed over the open face/side of the test reservoir, such that 12.5 cm$^2$ of the volatile material contact surface of the microporous sheet was exposed to the interior of the reservoir. The test reservoir was weighed to obtain an initial weight of the entire charged assembly. The test reservoir, containing benzyl acetate and enclosed with the sheet of microporous material, was then placed, standing upright, in a laboratory chemical fume hood having approximate dimensions of 5 feet [1.52 meters](height)×5 feet [1.52 meters](width)×2 feet [0.61 meters](depth). With the test reservoir standing upright, benzyl acetate was in direct contact with at least a portion of the volatile material contact surface of the microporous sheet. The glass doors of the fume hood were pulled down, and the air flow through the hood was adjusted so as to have eight (8) turns (or turnovers) of hood volume per hour. Unless otherwise indicated, the temperature in the hood was maintained at 25° C.±5° C. The humidity within in the fume hood was ambient. The test reservoirs were regularly weighed in the hood. The calculated weight loss of benzyl acetate, in combination with the elapsed time and surface area of the microporous sheet exposed to the interior of the test reservoir, were used to determine the volatile transfer rate of the microporous sheet, in units of mg/(hour*cm$^2$).

As used herein and in the claims, the percent increase in the volatile material transfer rate of the microporous material of the present invention from 25° C. to 60° C. was determined for separate but substantially equivalent microporous material sheet samples at 25° C. and 60° C., in accordance with the method described above. Reservoirs were placed in a large glass bell jar and over a 50% aqueous solution of potassium chloride also contained in the bell jar. The entire bell jar with contents was placed in an oven heated to 60° C. The reservoirs were held under these conditions for a period of 7 to 10 hours. The reservoirs were then returned to the hood at ambient conditions overnight and the process was repeated over several days. Each of the reservoirs was weighed before being placed in the bell jar and after being removed from the bell jar. Upon removal from the bell jar, the weight of each reservoir was taken after the reservoir had returned to ambient temperature.

As used herein and in the claims, the following method was used to determine if the vapor release surface of the microporous material is "substantially free of volatile material in liquid form". When the test reservoirs were weighed, as described above, the vapor release surface of the microporous sheet was examined visually by naked eye to determine if drops and/or a film of liquid were present thereon. If any evidence of drops (i.e., a single drop) and/or a film of liquid was visually observed on the vapor release surface, but did not run off the surface, the microporous sheet was considered to be acceptable. If the drops of volatile material liquid ran off the vapor release surface, the microporous sheet was determined to have failed. If no evidence of drops (i.e., not one drop) and/or a film of liquid was visually observed on the vapor release surface, the microporous sheet was determined to be substantially free of volatile material in liquid form.

Unless otherwise indicated, all ranges disclosed herein are to be understood to encompass any and all sub-ranges subsumed therein. For example, a stated range of "1 to 10" should be considered to include any and all sub-ranges between (and inclusive of) the minimum value of 1 and the maximum value of 10; that is, all subranges beginning with a minimum value of 1 or more and ending with a maximum value of 10 or less, e.g., 1 to 6.1, 3.5 to 7.8, 5.5 to 10, etc. Any numerical value, however, inherently contains certain errors necessarily resulting from the standard deviation found in its respective testing measurement, including that found in the measuring instrument.

Unless otherwise indicated, all numbers or expressions, such as those expressing structural dimensions, quantities of ingredients, etc., as used in the specification and claims, are understood as modified in all instances by the term "about." Accordingly, unless indicated to the contrary, the numerical parameters set forth in this specification and attached claims are approximations that can vary depending upon the desired results sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Further, as used in this specification and the attached claims, the singular forms "a", "an" and "the" are intended to include plural referents, unless expressly and unequivocally limited to one referent.

The term "volatile material", as used herein and in the claims, means a material that is capable of conversion to a gaseous or vapor form, i.e., capable of vaporizing, at ambient room temperature and pressure, and in the absence of imparted additional or supplementary energy, e.g., in the form of heat and/or agitation. The volatile material can comprise an organic volatile material, which can include those volatile materials comprising a solvent-based material, or those which are dispersed in a solvent-based material. The volatile material may be in a liquid form and/or in a solid form, and may be naturally occurring or synthetically formed. When in a solid form, the volatile material typically sublimes from the solid form to the vapor form without passing thru an intermediate liquid form. The volatile material may optionally be combined or formulated with non-volatile materials, such as a carrier, e.g., water and/or nonvolatile solvents. In the case of a solid volatile material, the nonvolatile carrier may be in the form of a porous material, e.g., a porous inorganic material, in which the solid volatile material is held. Also, the solid volatile material may be in the form of a semi-solid gel.

The volatile material may be a fragrance material, such as a naturally occurring or synthetic perfume oil. Examples of perfume oils from which the liquid volatile material may be selected include, but are not limited to, oil of bergamot, bitter orange, lemon, mandarin, caraway, cedar leaf, clove leaf, cedar wood, geranium, lavender, orange, origanum, petitgrain, white cedar, patchouli, neroili, rose absolute, and combinations thereof. Examples of solid fragrance materials from which the volatile material may be selected include, but are not limited to, vanillin, ethyl vanillin, coumarin, tonalid, calone, heliotropene, musk xylol, cedrol, musk ketone benzophenone, raspberry ketone, methyl naphthyl ketone beta, phenyl ethyl salicylate, veltol, maltol, maple lactone, proeugenol acetate, evemyl, and combinations thereof.

The volatile material transfer rate of the microporous material can be less than or equal to 0.7 mg/(hour*$cm^2$), or less than or equal to 0.6 mg/(hour*$cm^2$), or less than or equal to 0.55 mg/(hour*$cm^2$), or less than or equal to 0.50 mg/(hour*$cm^2$). The volatile material transfer rate of the microporous material can be equal to or greater than 0.02 mg/(hour*$cm^2$), or equal to or greater than 0.04 mg/(hour*$cm^2$), or equal to or greater than 0.30 mg/(hour*$cm^2$), or equal to or greater than 0.35 mg/(hour*$cm^2$). The volatile material transfer rate of the microporous material may range between any combination of these upper and lower values. For example, the volatile material transfer rate of the microporous material can be from 0.04 to 0.6 mg/(hour*$cm^2$), or from 0.2 to 0.6 mg/(hour*$cm^2$), or from 0.30 to 0.55 mg/(hour*$cm^2$), or from 0.35 to 0.50 mg/(hour*$cm^2$), in each case inclusive of the recited values.

While not intending to be bound by any theory, when volatile material is transferred from the volatile material contact surface to the vapor release surface of the microporous material, it is believed that the volatile material is in a form selected from liquid, vapor and a combination thereof. In addition, and without intending to be bound by any theory, it is believed that the volatile material, at least in part, moves through the network of interconnecting pores that communicate substantially throughout the microporous material. Typically, the transfer of volatile material occurs at temperatures of from 15° C. to 40° C., e.g., from 15 or 18° C. to 30 or 35° C. and at ambient atmospheric pressure.

The microporous material can have a density of at least 0.7 g/$cm^3$ or at least 0.8 g/$cm^3$. As used herein and in the claims, the density of the microporous material is determined by measuring the weight and volume of a sample of the microporous material. The upper limit of the density of the microporous material may range widely, provided it has a targeted volatile material transfer rate of, for example, from 0.04 to 0.6 mg/(hour*$cm^2$), and the vapor release surface is substantially free of volatile material in liquid form when volatile material is transferred from the volatile material contact surface to said vapor release surface. Typically, the density of the microporous material is less than or equal to 1.5 g/$cm^3$, or less than or equal to 1.0 g/$cm^3$. The density of the microporous material can range between any of the above-stated values, inclusive of the recited values. For example, the microporous material can have a density of from 0.7 g/$cm^3$ to 1.5 g/$cm^3$, such as, from 0.8 g/$cm^3$ to 1.2 g/$cm^3$, inclusive of the recited values.

When the microporous material has a density of at least 0.7 g/$cm^3$, such as at least 0.8 g/$cm^3$, the volatile material contact surface and the vapor release surface of the microporous material each may be free of a coating material thereon. When free of a coating material thereon, the volatile material contact surface and the vapor release surface each are defined by the microporous material.

When the microporous material has a density of at least 0.7 g/$cm^3$, such as at least 0.8 g/$cm^3$, at least a portion of the volatile material contact surface of the microporous material optionally may have a first coating thereon, and/or at least a portion of the vapor release surface of the microporous material optionally may have a second coating thereon. The first coating and the second coating may be the same or different. When at least a portion of the volatile material contact surface has a first coating thereon, the volatile material contact surface is defined at least in part by the first coating. When at least a portion of the vapor release surface has a second coating thereon, the vapor release surface is defined at least in part by the second coating.

The first coating and the second coating may each be formed from a coating selected from liquid coatings and solid particulate coatings (e.g., powder coatings). Typically, the first and second coatings each independently are formed from a coating selected from liquid coatings, which may optionally include a solvent selected from water, organic solvents and combinations thereof. The first and second coatings each independently may be selected from cross-linkable coatings, e.g., thermosetting coatings and photo-curable coatings, and non-crosslinkable coatings, e.g., air-dry coatings. The first and second coatings may be applied to the respective surfaces of the microporous material in accordance with art-recognized methods, such as spray application, curtain coating, dip coating, and/or drawn-down coating, e.g., by means of a doctor blade or draw-down bar, techniques.

The first and second coating compositions each independently can optionally include art-recognized additives, such as antioxidants, ultraviolet light stabilizers, flow control agents, dispersion stabilizers, e.g., in the case of aqueous dispersions, and colorants, e.g., dyes and/or pigments. Typically, the first and second coating compositions are free of colorants, and as such are substantially clear or opaque. Optional additives may be present in the coating compositions in individual amounts of from, for example, 0.01 to 10 percent by weight, based on the total weight of the coating composition.

The first coating and said second coating each independently can be formed from an aqueous coating composition that includes dispersed organic polymeric material. The aqueous coating composition may have a particle size of from 200 to 400 nm. The solids of the aqueous coating composition may vary widely, for example from 0.1 to 30 percent by weight, or from 1 to 20 percent by weight, in each case based on total weight of the aqueous coating composition. The organic polymers comprising the aqueous coating compositions may have number average molecular weights (Mn) of, for example, from 1000 to 4,000,000, or from 10,000 to 2,000,000.

The aqueous coating composition can be selected from aqueous poly(meth)acrylate dispersions, aqueous polyurethane dispersions, aqueous silicone (or silicon) oil dispersions, and combinations thereof. The poly(meth)acrylate polymers of the aqueous poly(meth)acrylate dispersions may be prepared in accordance with art-recognized methods. For example, the poly(meth)acrylate polymers may include residues (or monomer units) of alkyl (meth)acrylates having from 1 to 20 carbon atoms in the alkyl group. Examples of alkyl (meth)acrylates having from 1 to 20 carbon atoms in the alkyl group include, but are not limited to, methyl (meth)acrylate, ethyl (meth)acrylate, 2-hydroxyethyl (meth)acrylate, propyl (meth)acrylate, 2-hydroxypropyl (meth)acrylate, isopropyl (meth)acrylate, butyl (meth)acrylate, isobutyl (meth)acrylate, tert-butyl (meth)acrylate, 2-ethylhexyl (meth)acrylate, lauryl (meth)acrylate, isobornyl (meth)acrylate, cyclohexyl (meth)acrylate, and 3,3,5-trimethylcyclohexyl (meth)acrylate. For purposes of non-limiting illustration, an example of an aqueous poly(meth)acrylate dispersion from which the first and second coating compositions may each be independently selected is HYCAR 26138, which is commercially available from Lubrizol Advanced Materials, Inc.

The polyurethane polymers of the aqueous polyurethane dispersions, from which the first and second coatings each independently may be selected, include any of those known to the skilled artisan. Typically the polyurethane polymers are prepared from isocyanate functional materials having two or more isocyanate groups, and active hydrogen functional materials having two or more active hydrogen groups. The active hydrogen groups may be selected from, for example, hydroxyl groups, thiol groups, primary amines, secondary amines, and combinations thereof. For purposes of non-limiting illustration, an example of an aqueous polyurethane dispersion from which the first and second coating compositions may each be independently selected is WITCOBOND W-240, which is commercially available from Chemtura Corporation.

The silicon polymers of the aqueous silicone oil dispersions may be selected from known and art-recognized aqueous silicone oil dispersions. For purposes of non-limiting illustration, an example of an aqueous silicon dispersion from which the first and second coating compositions may each be independently selected is MOMENTIVE LE-410, which is commercially available from Momentive Performance Materials.

The first coating and the second coating each independently can be applied at any suitable thickness, provided the microporous material has a targeted volatile material transfer rate of, for example, from 0.04 to 0.6 mg/(hour*cm$^2$), and the vapor release surface is substantially free of volatile material in liquid form when volatile material is transferred from the volatile material contact surface to said vapor release surface. Also, the first coating and the second coating each independently can have a coating weight, i.e., the weight of the coating which is on the microporous material, of from 0.01 to 5.5 g/m$^2$, such as from 0.1 to 5.0 g/m$^2$, or from 0.5 to 3 g/m$^2$, or from 0.75 to 2.5 g/m$^2$, or from 1 to 2 g/m$^2$.

The microporous material can have a density of less than 0.8 g/cm$^3$, and at least a portion of the volatile material contact surface of the microporous material can have a first coating thereon, and/or at least a portion of the vapor release surface of the microporous material can have a second coating thereon. The first coating and the second coating may be the same or different, and are each independently as described previously herein with regard to the optional first and second coatings of the microporous material having a density of at least 0.8 g/cm$^3$.

When less than 0.8 g/cm$^3$, the density of the microporous material of the present invention may have any suitable lower limit, provided the microporous material has a targeted volatile material transfer rate of, for example, from 0.04 to 0.6 mg/(hour*cm$^2$), and the vapor release surface is substantially free of volatile material in liquid form when volatile material is transferred from the volatile material contact surface to said vapor release surface. With this particular embodiment of the present invention, the density of the microporous material may be from 0.6 to less than 0.8 g/cm$^3$, or from 0.6 to 0.75 g/cm$^3$, e.g., from 0.60 to 0.75 g/cm$^3$, or from 0.6 to 0.7 g/cm$^3$, e.g., from 0.60 to 0.70 g/cm$^3$, or from 0.65 to 0.70 g/cm$^3$.

Further, at least a portion of the volatile material contact surface of the microporous material can have a first coating thereon, and/or at least a portion of the vapor release surface of the microporous material can have a second coating thereon, in which the first and second coatings each independently are selected from a coating composition comprising a poly(vinyl alcohol).

With the poly(vinyl alcohol) coated embodiment of the present invention, when the microporous material, i.e., the poly(vinyl alcohol) coated microporous material, is exposed to a temperature increase of from 25° C. to 60° C., the volatile material transfer rate thereof increases by less than or equal 150 percent. When the poly(vinyl alcohol) coated microporous material is exposed to a temperature increase, e.g., from an ambient temperature of from 25° C. to 60° C., the volatile material transfer rate typically increases, and typically does not decrease unless, for example, the microporous material has been damaged by exposure to the higher ambient temperature. As such, and as used herein and in the claims, the statement "the volatile material transfer rate thereof increases by less than or equal to [a stated] percent", e.g., 150 percent, is inclusive of a lower limit of 0 percent, but is not inclusive of a lower limit that is less than 0 percent.

For purposes of illustration, when the poly(vinyl alcohol) coated microporous material has a volatile material transfer rate of 0.3 mg/(hour*cm$^2$) at 25° C., and when the microporous material is exposed to a temperature of 60° C., the volatile material transfer rate increases to a value that is less than or equal to 0.75 mg/(hour*cm$^2$).

In an embodiment when the microporous material, i.e., the poly(vinyl alcohol) coated microporous material, is exposed to a temperature increase of from 25° C. to 60° C., the volatile material transfer rate thereof increases by less than or equal to 125 percent. For example, when the poly(vinyl alcohol) coated microporous material has a volatile material transfer rate of 0.3 mg/(hour*cm$^2$) at 25° C., and when the microporous material is exposed to a temperature of 60° C., the volatile material transfer rate increases to a value that is less than or equal to 0.68 mg/(hour*cm$^2$).

Further, when the microporous material, i.e., the poly(vinyl alcohol) coated microporous material, is exposed to a temperature increase of from 25° C. to 600° C., the volatile material transfer rate thereof increases by less than or equal 100 percent. For example, when the poly(vinyl alcohol) coated microporous material has a volatile material transfer rate of 0.3 mg/(hour*cm$^2$) at 25° C., and when the microporous material is exposed to a temperature of 60° C., the volatile material transfer rate increases to a value that is less than or equal to 0.6 mg/(hour*cm$^2$).

The first and second poly(vinyl alcohol) coatings may each be independently present in any suitable coating weight, provided the microporous material has a targeted volatile material transfer rate of, for example, at least 0.04 mg/(hour*cm$^2$), and when the microporous material, i.e., the poly(vinyl alcohol) coated microporous material, is exposed to a temperature increase of from 25° C. to 60° C., the volatile material transfer rate thereof increases by less than or equal to 150 percent. Typically, the first poly(vinyl alcohol) coating and the second poly(vinyl alcohol) coating each independently have a coating weight of from 0.01 to 5.5 g/m$^2$, or from 0.1 to 4.0 g/m$^2$, or from 0.5 to 3.0 g/m$^2$, or from 0.75 to 2.0 g/m$^2$.

The volatile material transfer rate of the poly(vinyl alcohol) coated microporous material can be at least 0.02 mg/(hour*cm$^2$). The volatile material transfer rate of the poly(vinyl alcohol) coated microporous material may be equal to or greater than 0.04 mg/(hour*cm$^2$), or equal to or greater than 0.1 mg/(hour*cm$^2$), or equal to or greater than 0.2 mg/(hour*cm$^2$), or equal to or greater than 0.30 mg/(hour*cm$^2$), or equal to or greater than 0.35 mg/(hour*cm$^2$). The volatile material transfer rate of the poly(vinyl alcohol) coated microporous material may be less than or equal to 0.7 mg/(hour*cm$^2$), or less than or equal to 0.6 mg/(hour*cm$^2$), or less than or equal to 0.55 mg/(hour*cm$^2$), or less than or equal to 0.50 mg/(hour*cm$^2$). The volatile material transfer rate of the poly(vinyl alcohol) coated microporous material may range between any combination of these upper and lower values, inclusive of the recited values. For example, the volatile material transfer rate of the poly(vinyl alcohol) coated microporous material can be at least 0.02 mg/(hour*cm$^2$), such as from 0.04 to 0.70 mg/(hour*cm$^2$), or from 0.04 to 0.60 mg/(hour*cm$^2$), or from 0.20 to 0.60 mg/(hour*cm$^2$), or from 0.30 to 0.55 mg/(hour*cm$^2$), or from 0.35 to 0.50 mg/(hour*cm$^2$), in each case inclusive of the recited values.

The density of the microporous material of the poly(vinyl alcohol) coated microporous material embodiment of the present invention may vary widely, provided that the poly(vinyl alcohol) coated microporous material has a targeted volatile material transfer rate, for example, of at least 0.04 mg/(hour*cm$^2$), and when the microporous material, i.e., the poly(vinyl alcohol) coated microporous material, is exposed to a temperature increase of from 25° C. to 60° C., the volatile material transfer rate thereof increases by less than or equal to 150 percent.

Further, the density of the microporous material, of the poly(vinyl alcohol) coated microporous material, may be at least 0.7 g/cm$^3$, such as at least 0.8 g/cm$^3$, e.g., from 0.8 to 1.2 g/cm$^3$, all inclusive of the recited values. In an embodiment of the present invention, the density of the poly(vinyl alcohol) coated microporous material, i.e., the density of the microporous material prior to application of the poly(vinyl alcohol) coating, is less than 0.8 g/cm$^3$. For example, the density of the microporous material, of the poly(vinyl alcohol) coated microporous material, may be from 0.6 to less than 0.8 g/cm$^3$, or from 0.6 to 0.75 g/cm$^3$, e.g., from 0.60 to 0.75 g/cm$^3$, or from 0.6 to 0.7 g/cm$^3$, e.g., from 0.60 to 0.70 g/cm$^3$, or from 0.65 to 0.70 g/cm$^3$, all inclusive of the recited values.

With regard to the poly(vinyl alcohol) coated microporous material of the present invention, when volatile material is transferred from the volatile material contact surface to the vapor release surface, the vapor release surface is substantially free of volatile material in liquid form.

The poly(vinyl alcohol) coating may be selected from liquid coatings which may optionally include a solvent selected from water, organic solvents and combinations thereof. The poly(vinyl alcohol) coating may be selected from crosslinkable coatings, e.g., thermosetting coatings, and non-crosslinkable coatings, e.g., air-dry coatings. The poly(vinyl alcohol) coating may be applied to the respective surfaces of the microporous material in accordance with art-recognized methods, such as spray application, curtain coating, or drawn-down coating, e.g., by means of a doctor blade or draw-down bar.

In an embodiment, the first and second poly(vinyl alcohol) coatings are each independently formed from aqueous poly(vinyl alcohol) coating compositions. The solids of the aqueous poly(vinyl alcohol) coating composition may vary widely, for example from 0.1 to 15 percent by weight, or from 0.5 to 9 percent by weight, in each case based on total weight of the aqueous coating composition. The poly(vinyl alcohol) polymer of the poly(vinyl alcohol) coating compositions may have number average molecular weights (Mn) of, for example, from 100 to 1,000,000, or from 1000 to 750,000.

The poly(vinyl alcohol) polymer of the poly(vinyl alcohol) coating composition may be a homopolymer or copolymer. Comonomers from which the poly(vinyl alcohol) copolymer may be prepared include those which are copolymerizable (by means of radical polymerization) with vinyl acetate, and which are known to the skilled artisan. For purposes of illustration, comonomers from which the poly(vinyl alcohol) copolymer may be prepared include, but are not limited to: (meth)acrylic acid, maleic acid, fumaric acid, crotonic acid, metal salts thereof, alkyl esters thereof, e.g., $C_2$-$C_{10}$ alkyl esters thereof, polyethylene glycol esters thereof, and polypropylene glycol esters thereof; vinyl chloride; tetrafluoroethylene; 2-acrylamido-2-methyl-propane sulfonic acid and its salts; acrylamide; N-alkyl acrylamide; N,N-dialkyl substituted acrylamides; and N-vinyl formamide.

For purposes of non-limiting illustration, an example of a poly(vinyl alcohol) coating composition that may be used to form the poly(vinyl alcohol) coated microporous material of the present invention is CELVOL 325, which is commercially available from Sekisui Specialty Chemicals.

The first and second poly(vinyl alcohol) coating compositions may each independently include art-recognized additives, such as antioxidants, ultraviolet light stabilizers, flow control agents, dispersion stabilizers, e.g., in the case of aqueous dispersions, and colorants, e.g., dyes and/or pigments. Typically, the first and second poly(vinyl alcohol) coating compositions are free of colorants, and are as such substantially clear or opaque. Optional additives may be present in the poly(vinyl alcohol) coating compositions in individual amounts of from, for example, 0.01 to 10 percent by weight, based on the total weight of the coating composition.

The matrix of the microporous material is composed of substantially water-insoluble thermoplastic organic polymer. The numbers and kinds of such polymers suitable for use as the matrix are large. In general, any substantially water-insoluble thermoplastic organic polymer which can be extruded, calendered, pressed, or rolled into film, sheet, strip, or web may be used. The polymer may be a single polymer or it may be a mixture of polymers. The polymers may be homopolymers, copolymers, random copolymers, block copolymers, graft copolymers, atactic polymers, isotactic polymers, syndiotactic polymers, linear polymers, or branched polymers. When mixtures of polymers are used, the mixture may be homogeneous or it may comprise two or more polymeric phases.

Examples of classes of suitable substantially water-insoluble thermoplastic organic polymers include thermoplastic polyolefins, poly(halo-substituted olefins), polyesters, polyamides, polyurethanes, polyureas, poly(vinyl halides), poly(vinylidene halides), polystyrenes, poly(vinyl esters), polycarbonates, polyethers, polysulfides, polyimides, polysilanes, polysiloxanes, polycaprolactones, polyacrylates, and polymethacrylates. Contemplated hybrid classes, from which the substantially water-insoluble thermoplastic organic polymers may be selected include, for example, thermoplastic poly(urethane-ureas), poly(ester-amides), poly(silane-siloxanes), and poly(ether-esters). Further examples of suitable substantially water-insoluble thermoplastic organic polymers include thermoplastic high density polyethylene, low density polyethylene, ultrahigh molecular weight polyethylene, polypropylene (atactic, isotactic, or syndiotactic), poly(vinyl chloride), polytetrafluoroethylene, copolymers of ethylene and acrylic acid, copolymers of ethylene and methacrylic acid, poly(vinylidene chloride), copolymers of vinylidene chloride and vinyl acetate, copolymers of vinylidene chloride and vinyl chloride, copolymers of ethylene and propylene, copolymers of ethylene and butene, poly(vinyl acetate), polystyrene, poly(omega-aminoundecanoic acid) poly(hexamethylene adipamide), poly (epsilon-caprolactam), and poly(methyl methacrylate). The recitation of these classes and example of substantially water-insoluble thermoplastic organic polymers is not exhaustive, and are provided only for purposes of illustration.

Substantially water-insoluble thermoplastic organic polymers may in particular include, for example, poly(vinyl chloride), copolymers of vinyl chloride, or mixtures thereof. In an embodiment, the water-insoluble thermoplastic organic polymer includes an ultrahigh molecular weight polyolefin selected from: ultrahigh molecular weight polyolefin, e.g., essentially linear ultrahigh molecular weight polyolefin) having an intrinsic viscosity of at least 10 deciliters/gram; or ultrahigh molecular weight polypropylene, e.g., essentially linear ultrahigh molecular weight polypropylene) having an intrinsic viscosity of at least 6 deciliters/gram; or mixtures thereof. In a particular embodiment, the water-insoluble thermoplastic organic polymer includes ultrahigh molecular weight polyethylene, e.g., linear ultrahigh molecular weight polyethylene, having an intrinsic viscosity of at least 18 deciliters/gram.

Ultrahigh molecular weight polyethylene (UHMWPE) is not a thermoset polymer having an infinite molecular weight, but is technically classified as a thermoplastic. However, because the molecules are substantially very long chains, UHMWPE softens when heated but does not flow as a molten liquid in a normal thermoplastic manner. The very long chains and the peculiar properties they provide to UHMWPE are believed to contribute in large measure to the desirable properties of microporous materials made using this polymer.

As indicated earlier, the intrinsic viscosity of the UHMWPE is at least about 10 deciliters/gram. Usually the intrinsic viscosity is at least about 14 deciliters/gram. Often the intrinsic viscosity is at least about 18 deciliters/gram. In many cases the intrinsic viscosity is at least about 19 deciliters/gram. Although there is no particular restriction on the upper limit of the intrinsic viscosity, the intrinsic viscosity is frequently in the range of from about 10 to about 39 deciliters/gram, e.g., in the range of from about 14 to about 39 deciliters/gram. In most cases the intrinsic viscosity of the UHMWPE is in the range of from about 18 to about 39 deciliters/gram, typically from about 18 to about 32 deciliters/gram.

The nominal molecular weight of UHMWPE is empirically related to the intrinsic viscosity of the polymer according to the equation:

$$M(\text{UHMWPE}) = 5.3 \times 10^4 [\eta]^{1.37}$$

where M(UHMWPE) is the nominal molecular weight and [η] is the intrinsic viscosity of the UHMW polyethylene expressed in deciliters/gram.

As used herein and in the claims, intrinsic viscosity is determined by extrapolating to zero concentration the reduced viscosities or the inherent viscosities of several dilute solutions of the UHMWPE where the solvent is freshly distilled decahydronaphthalene to which 0.2 percent by weight, 3,5-di-tert-butyl-4-hydroxyhydrocinnamic acid, neopentanetetrayl ester [CAS Registry No. 6683-19-8] has been added. The reduced viscosities or the inherent viscosities of the UHMWPE are ascertained from relative viscosities obtained at 135 degree C. using an Ubbelohde No. 1 viscometer in accordance with the general procedures of ASTM D 4020-81, except that several dilute solutions of differing concentration are employed. ASTM D 4020-81 is, in its entirety, incorporated herein by reference.

In one particular embodiment, the matrix comprises a mixture of substantially linear ultrahigh molecular weight polyethylene having an intrinsic viscosity of at least 10 deciliters/gram, and lower molecular weight polyethylene (LMWPE) having an ASTM D 1238-86 Condition E melt index of less than 50 grams/10 minutes and an ASTM D 1238-86 Condition F melt index of at least 0.1 gram/10 minutes. The nominal molecular weight of LMWPE is lower than that of the UHMW polyethylene. LMWPE is thermoplastic and many different types are known. One method of classification is by density, expressed in grams/cubic centimeter and rounded to the nearest thousandth, in accordance with ASTM D 1248-84 (re-approved 1989), as summarized as follows:

| Type | Abbreviation | Density (g/cm³) |
|---|---|---|
| Low Density Polyethylene | LDPE | 0.910-0.925 |
| Medium Density Polyethylene | MDPE | 0.926-0.940 |
| High Density Polyethylene | HDPE | 0.941-0.965 |

Any or all of these polyethylenes may be used as the LMWPE in the present invention. For some applications, HDPE, may be used because it ordinarily tends to be more linear than MDPE or LDPE. ASTM D 1248-84 (Reapproved 1989) is, in its entirety, incorporated herein by reference.

Processes for making the various LMWPE's are well known and well documented. They include the high pressure process, the Phillips Petroleum Company process, the Standard Oil Company (Indiana) process, and the Ziegler process.

The ASTM D 1238-86 Condition E (that is, 190 degree C. and 2.16 kilogram load) melt index of the LMWPE is less than about 50 grams/10 minutes. Often the Condition E melt index is less than about 25 grams/10 minutes. Typically, the Condition E melt index is less than about 15 grams/10 minutes.

The ASTM D 1238-86 Condition F (that is, 190 degree C. and 21.6 kilogram load) melt index of the LMWPE is at least 0.1 gram/10 minutes. In many cases the Condition F melt index is at least about 0.5 gram/10 minutes. Typically, the Condition F melt index is at least about 1.0 gram/10 minutes. ASTM D 1238-86 is, in its entirety, incorporated herein by reference.

Sufficient UHMWPE and LMWPE should be present in the matrix to provide their properties to the microporous material. Other thermoplastic organic polymers may also be present in the matrix so long as their presence does not materially affect the properties of the microporous material in an adverse manner. One or more other thermoplastic polymers may be present in the matrix. The amount of the other thermoplastic polymer which may be present depends upon the nature of such polymer. Examples of thermoplastic organic polymers which may optionally be present include, but are not limited to, poly(tetrafluoroethylene), polypropylene, copolymers of ethylene and propylene, copolymers of ethylene and acrylic acid, and copolymers of ethylene and methacrylic acid. If desired, all or a portion of the carboxyl groups of carboxyl-containing copolymers may be neutralized with sodium, zinc, or the like.

In most cases the UHMWPE and the LMWPE together constitute at least about 65 percent by weight of the polymer of the matrix. Often the UHMWPE and the LMWPE together constitute at least about 85 percent by weight of the polymer of the matrix. Typically, the other thermoplastic organic polymers are substantially absent so that the UHMWPE and the LMWPE together constitute substantially 100 percent by weight of the polymer of the matrix.

The UHMWPE can constitute at least one percent by weight of the polymer of the matrix. Where the UHMWPE and the LMWPE together constitute 100 percent by weight of the polymer of the matrix of the microporous material, the UHMWPE can constitute greater than or equal to 40 percent by weight of the polymer of the matrix, such as greater than or equal to 45 percent by weight, or greater than or equal to 48 percent by weight, or greater than or equal to 50 percent by weight, or greater than or equal to 55 percent by weight of the polymer of the matrix. Also, the UHMWPE can constitute less than or equal to 99 percent by weight of the polymer of the matrix, such as less than or equal to 80 percent by weight, or less than or equal to 70 percent by weight, or less than or equal to 65 percent by weight, or less than or equal to 60 percent by weight of the polymer of the matrix. The level of UHMWPE comprising the polymer of the matrix can range between any of these values inclusive of the recited values.

Likewise, where the UHMWPE and the LMWPE together constitute 100 percent by weight of the polymer of the matrix of the microporous material, the LMWPE can constitute greater than or equal to 1 percent by weight of the polymer of the matrix, such as greater than or equal to 5 percent by weight, or greater than or equal to 10 percent by weight, or greater than or equal to 15 percent by weight, or greater than or equal to 20 percent by weight, or greater than or equal to 25 percent by weight, or greater than or equal to 30 percent by weight, or greater than or equal to 35 percent by weight, or greater than or equal to 40 percent by weight, or greater than or equal to 45 percent by weight, or greater than or equal to 50 percent by weight, or greater than or equal to 55 percent by weight of the polymer of the matrix. Also, the LMWPE can constitute less than or equal to 70 percent by weight of the polymer of the matrix, such as less than or equal to 65 percent by weight, or less than or equal to 60 percent by weight, or less than or equal to 55 percent by weight, or less than or equal to 50 percent by weight, or less than or equal to 45 percent by weight of the polymer of the matrix. The level of the LMWPE can range between any of these values inclusive of the recited values.

It should be noted that for any of the previously described microporous materials of the present invention, the LMWPE can comprise high density polyethylene.

The microporous material also includes a finely-divided, substantially water-insoluble particulate filler material. The particulate filler material may include an organic particulate material and/or an inorganic particulate material. The particulate filler material typically is not colored, for example, the particulate filler material is a white or off-white particulate filler material, such as a siliceous or clay particulate material.

The finely divided substantially water-insoluble filler particles may constitute from 20 to 90 percent by weight of the microporous material. For example, such filler particles may constitute from 30 percent to 90 percent by weight of the microporous material, or from 40 to 90 percent by weight of the microporous material, or from 40 to 85, e.g., 45 to 80, percent by weight of the microporous material, or from 50 to 80, e.g., 50 to 65, 70 or 75, percent by weight of the microporous material and even from 60 percent to 90 percent by weight of the microporous material.

The finely divided substantially water-insoluble particulate filler may be in the form of ultimate particles, aggregates of ultimate particles, or a combination of both. At least about 90 percent by weight of the filler used in preparing the microporous material has gross particle sizes in the range of from 0.5 to about 200 micrometers, such as from 1 to 100 micrometers, as determined by the use of a laser diffraction particle size instrument, LS230 from Beckman Coulton, which is capable of measuring particle diameters as small as 0.04 micrometers. Typically, at least 90 percent by weight of the particulate filler has gross particle sizes in the range of from 5 to 40, e.g., 10 to 30 micrometers. The sizes of the filler agglomerates may be reduced during processing of the ingredients used to prepare the microporous material. Accordingly, the distribution of gross particle sizes in the microporous material may be smaller than in the raw filler itself.

Non-limiting examples of suitable organic and inorganic particulate materials, that may be used in the microporous material of the present invention, include those described in U.S. Pat. No. 6,387,519 B1 at column 9, line 4 to column 13, line 62, the cited portions of which are incorporated herein by reference.

In a particular embodiment of the present invention, the particulate filler material comprises siliceous materials. Non-limiting examples of siliceous fillers that may be used to prepare the microporous material include silica, mica, montmorillonite, kaolinite, nanoclays such as cloisite, which is available from Southern Clay Products, talc, diatomaceous earth, vermiculite, natural and synthetic zeolites, calcium silicate, aluminum silicate, sodium aluminum silicate, aluminum polysilicate, alumina silica gels and glass particles. In addition to the siliceous fillers, other finely divided particulate substantially water-insoluble fillers optionally may also be employed. Non-limiting examples of such optional particulate fillers include carbon black, charcoal, graphite, titanium oxide, iron oxide, copper oxide, zinc oxide, antimony oxide, zirconia, magnesia, alumina, molybdenum disulfide, zinc sulfide, barium sulfate, strontium sulfate, calcium carbonate, and magnesium carbonate. Some of such optional fillers are color-producing fillers and, depending on the amount used, may add a hue or color to the microporous material. In a non-limiting embodiment, the siliceous filler may include silica and any of the aforementioned clays. Non-limiting examples of silicas include precipitated silica, silica gel, fumed silica, and combinations thereof.

Silica gel is generally produced commercially by acidifying an aqueous solution of a soluble metal silicate, e.g., sodium silicate, at low pH with acid. The acid employed is generally a strong mineral acid such as sulfuric acid or hydrochloric acid, although carbon dioxide can be used. Inasmuch as there is essentially no difference in density between the gel phase and the surrounding liquid phase while the viscosity is low, the gel phase does not settle out, that is to say, it does not precipitate. Consequently, silica gel may be described as a non-precipitated, coherent, rigid, three-dimensional network of contiguous particles of colloidal amorphous silica. The state of subdivision ranges from large, solid masses to submicroscopic particles, and the degree of hydration from almost anhydrous silica to soft gelatinous masses containing on the order of 100 parts of water per part of silica by weight.

Precipitated silica generally is produced commercially by combining an aqueous solution of a soluble metal silicate, ordinarily alkali metal silicate such as sodium silicate, and an acid so that colloidal particles of silica will grow in a weakly alkaline solution and be coagulated by the alkali metal ions of the resulting soluble alkali metal salt. Various acids may be used, including but not limited to mineral acids. Non-limiting examples of acids that may be used include hydrochloric acid and sulfuric acid, but carbon dioxide can also be used to produce precipitated silica. In the absence of a coagulant, silica is not precipitated from solution at any pH. In a non-limiting embodiment, the coagulant used to effect precipitation of silica may be the soluble alkali metal salt produced during formation of the colloidal silica particles, or it may be an added electrolyte, such as a soluble inorganic or organic salt, or it may be a combination of both.

Many different precipitated silicas can be employed as the siliceous filler used to prepare the microporous material. Precipitated silicas are well-known commercial materials, and processes for producing them are described in detail in many United States patents, including U.S. Pat. Nos. 2,940,830 and 4,681,750. The average ultimate particle size (irrespective of whether or not the ultimate particles are agglomerated) of precipitated silica used to prepare the microporous material is generally less than 0.1 micrometer, e.g., less than 0.05 micrometer or less than 0.03 micrometer, as determined by transmission electron microscopy. Precipitated silicas are available in many grades and forms from PPG Industries, Inc. These silicas are sold under the Hi-Sil® trademark.

For purposes of the present invention, the finely divided particulate substantially water-insoluble siliceous filler can comprise at least 50 percent by weight, e.g., at least 65 or at least 75 percent by weight, or at least 90 percent by weight of the substantially water-insoluble filler material. The siliceous filler may comprise from 50 to 90 percent by weight, e.g., from 60 to 80 percent by weight, of the particulate filler material, or the siliceous filler may comprise substantially all of the substantially water-insoluble particulate filler material.

The particulate filler, e.g., the siliceous filler, typically has a high surface area, which allows the filler to carry much of the processing plasticizer composition used to produce the microporous material of the present invention. High surface area fillers are materials of very small particle size, materials that have a high degree of porosity, or materials that exhibit both of such properties. The surface area of the particulate filler, e.g., the siliceous filler particles, can range from 20 or 40 to 400 square meters per gram, e.g., from 25 to 350 square meters per gram, or from 40 to 160 square meters per gram, as determined by the Brunauer, Emmett, Teller (BET) method according to ASTM D 1993-91. The BET surface area is determined by fitting five relative pressure points from a nitrogen sorption isotherm measurement made using a Micromeritics TriStar 3000™ instrument. A FlowPrep-060™ station can be used to provide heat and continuous gas flow during sample preparation. Prior to nitrogen sorption, silica samples are dried by heating to 160° C. in flowing nitrogen (PS) for 1 hour. Generally, but not necessarily, the surface area of any non-siliceous filler particles used is also within one of these ranges. The filler particles are substantially water-insoluble and also can be substantially insoluble in any organic processing liquid used to prepare the microporous material. This can facilitate retention of the particulate filler within the microporous material.

The microporous material of the present may also include minor amounts, e.g., less than or equal to 5 percent by weight, based on total weight of the microporous material, of other materials used in processing, such as lubricant, processing plasticizer, organic extraction liquid, water, and the like. Further materials introduced for particular purposes, such as thermal, ultraviolet and dimensional stability, may optionally be present in the microporous material in small amounts, e.g., less than or equal to 15 percent by weight, based on total weight of the microporous material. Examples of such further materials include, but are not limited to, antioxidants, ultraviolet light absorbers, reinforcing fibers such as chopped glass fiber strand, and the like. The balance of the microporous material, exclusive of filler and any coating, printing ink, or impregnant applied for one or more special purposes is essentially the thermoplastic organic polymer.

The microporous material of the present invention, also includes a network of interconnecting pores, which communicate substantially throughout the microporous material. On a coating-free, printing ink free and impregnant-free basis, pores typically constitute from 35 to 95 percent by volume, based on the total volume of the microporous material, when made by the processes as further described herein. The pores may constitute from 60 to 75 percent by volume of the microporous material, based on the total volume of the microporous material. As used herein and in the claims, the porosity (also known as void volume) of the microporous material, expressed as percent by volume, is determined according to the following equation:

$$\text{Porosity} = 100[1 - d_1/d_2]$$

where, $d_1$ is the density of the sample, which is determined from the sample weight and the sample volume as ascertained from measurements of the sample dimensions; and $d_2$ is the density of the solid portion of the sample, which is determined from the sample weight and the volume of the solid portion of the sample. The volume of the solid portion of the microporous material is determined using a Quantachrome stereopycnometer (Quantachrome Corp.) in accordance with the operating manual accompanying the instrument.

The volume average diameter of the pores of the microporous material is determined by mercury porosimetry using an Autoscan mercury porosimeter (Quantachrome Corp.) in accordance with the operating manual accompanying the instrument. The volume average pore radius for a single scan is automatically determined by the porosimeter. In operating the porosimeter, a scan is made in the high pressure range (from 138 kilopascals absolute to 227 megapascals absolute). If 2 percent or less of the total intruded volume occurs at the low end (from 138 to 250 kilopascals absolute) of the high pressure range, the volume average pore diameter is taken as twice the volume average pore radius determined by the porosimeter. Otherwise, an additional scan is made in the low pressure range (from 7 to 165 kilopascals absolute) and the volume average pore diameter is calculated according to the equation:

$$d=2[v_1r_1/w_1+v_2r_2/w_2]/[v_1/w_1+v_2/w_2]$$

where, d is the volume average pore diameter; $v_1$ is the total volume of mercury intruded in the high pressure range; $v_2$ is the total volume of mercury intruded in the low pressure range; $r_1$ is the volume average pore radius determined from the high pressure scan; $r_2$ is the volume average pore radius determined from the low pressure scan; $w_3$ is the weight of the sample subjected to the high pressure scan; and $w_2$ is the weight of the sample subjected to the low pressure scan.

Generally on a coating-free, printing ink-free and impregnant-free basis, the volume average diameter of the pores of the microporous material is at least 0.02 micrometers, typically at least 0.04 micrometers, and more typically at least 0.05 micrometers. On the same basis, the volume average diameter of the pores of the microporous material is also typically less than or equal to 0.5 micrometers, more typically less than or equal to 0.3 micrometers, and further typically less than or equal to 0.25 micrometers. The volume average diameter of the pores, on this basis, may range between any of these values, inclusive of the recited values. For example, the volume average diameter of the pores of the microporous material may range from 0.02 to 0.5 micrometers, or from 0.04 to 0.3 micrometers, or from 0.05 to 0.25 micrometers, in each case inclusive of the recited values.

In the course of determining the volume average pore diameter by means of the above described procedure, the maximum pore radius detected may also be determined. This is taken from the low pressure range scan, if run; otherwise it is taken from the high pressure range scan. The maximum pore diameter of the microporous material is typically twice the maximum pore radius.

Coating, printing and impregnation processes can result in filling at least some of the pores of the microporous material. In addition, such processes may also irreversibly compress the microporous material. Accordingly, the parameters with respect to porosity, volume average diameter of the pores, and maximum pore diameter are determined for the microporous material prior to application of one or more of these processes.

Numerous art-recognized processes may be used to produce the microporous materials of the present invention. For example, the microporous material of the present invention can be prepared by mixing together filler particles, thermoplastic organic polymer powder, processing plasticizer and minor amounts of lubricant and antioxidant, until a substantially uniform mixture is obtained. The weight ratio of particulate filler to polymer powder employed in forming the mixture is essentially the same as that of the microporous material to be produced. The mixture, together with additional processing plasticizer, is typically introduced into the heated barrel of a screw extruder. Attached to the terminal end of the extruder is a sheeting die. A continuous sheet formed by the die is forwarded without drawing to a pair of heated calender rolls acting cooperatively to form a continuous sheet of lesser thickness than the continuous sheet exiting from the die. The level of processing plasticizer present in the continuous sheet at this point in the process can vary and will effect the density of the final microporous sheet. For example, the level of processing plasticizer present in the continuous sheet, prior to extraction as described herein below, can be greater than or equal to 30 percent by weight of the continuous sheet, such as greater than or equal to 40 percent by weight, or greater than or equal to 45 percent by weight of the continuous sheet prior to extraction. Also, the amount of processing plasticizer present in the continuous sheet prior to extraction can be less than or equal to 70 percent by weight of the continuous sheet, such as less than or equal to 65 percent by weight, or less than or equal to 60 percent by weight, or less than or equal to 57 percent by weight of the continuous sheet prior to extraction. The level of processing plasticizer present in the continuous sheet at this point in the process, prior to extraction, can range between any of these values inclusive of the recited values. Generally, the level of processing plasticizer can in one embodiment vary from 57 to 62 weight percent, and in another embodiment be less than 57 weight percent.

The continuous sheet from the calender is then passed to a first extraction zone where the processing plasticizer is substantially removed by extraction with an organic liquid, which is a good solvent for the processing plasticizer, a poor solvent for the organic polymer, and more volatile than the processing plasticizer. Usually, but not necessarily, both the processing plasticizer and the organic extraction liquid are substantially immiscible with water. The continuous sheet then passes to a second extraction zone where residual organic extraction liquid is substantially removed by steam and/or water. The continuous sheet is then passed through a forced air dryer for substantial removal of residual water and remaining residual organic extraction liquid. From the dryer the continuous sheet, which is microporous material, is passed to a take-up roll.

The processing plasticizer is a liquid at room temperature and usually is a processing oil such as paraffinic oil, naphthenic oil, or aromatic oil. Suitable processing oils include those meeting the requirements of ASTM D 2226-82. Types 103 and 104. More typically, processing oils having a pour point of less than 220° C. according to AS1M D 97-66 (re-approved 1978) are used to produce the microporous material of the present invention. Processing plasticizers useful in preparing the microporous material of the present invention are discussed in further detail in U.S. Pat. No. 5,326,391 at column 10, lines 26 through 50, which disclosure is incorporated herein by reference.

In an embodiment of the present invention, the processing plasticizer composition used to prepare the microporous material has little solvating effect on the polyolefin at 60° C., and only a moderate solvating effect at elevated temperatures on the order of 100° C. The processing plasticizer composition generally is a liquid at room temperature.

Non-limiting examples of processing oils that may be used can include SHELLFLEX® 412 oil, SHELLFLEX® 371 oil (Shell Oil Co.), which are solvent refined and hydrotreated oils derived from naphthenic crude oils, ARCOprimeX® 400 oil (Atlantic Richfield Co.) and KAYDOL® oil (Witco Corp.), which are white mineral oils. Other non-limiting examples of processing plasticizers can include phthalate ester plasticizers, such as dibutyl phthalate, bis(2-ethylhexyl) phthalate, diisodecyl phthalate, dicyclohexyl phthalate, butyl benzyl phthalate, and ditridecyl phthalate. Mixtures of any of the foregoing processing plasticizers can be used to prepare the microporous material of the present invention.

There are many organic extraction liquids that can be used to prepare the microporous material of the present invention. Examples of suitable organic extraction liquids include those described in U.S. Pat. No. 5,326,391 at column 10, lines 51 through 57, which disclosure is incorporated herein by reference.

The extraction fluid composition can comprise halogenated hydrocarbons, such as chlorinated hydrocarbons and/or fluorinated hydrocarbons. In particular, the extraction fluid composition may include halogenated hydrocarbon(s) and have a calculated solubility parameter coulomb term ($\delta$clb) ranging from 4 to 9 $(Jcm^3)^{1/2}$. Non-limiting examples of halogenated hydrocarbon(s) suitable as the extraction fluid composition for use in producing the microporous material of the present invention can include one or more azeotropes of halogenated hydrocarbons selected from trans-1,2-dichloroethylene, 1,1,1,2,2,3,4,5,5,5-decafluoropentane, and/or 1,1,1,3,3-pentafluorobutane. Such materials are available commercially as VERTREL MCA (a binary azeotrope of 1,1,1,2,2,3,4,5,5,5-dihydrodecafluoropentane and trans-1,2-dichloroethylene: 62%/38%), and VERTREL CCA (a ternary azeotrope of 1,1,1,2,2,3,4,5,5,5-dihydrodecafluorpentane, 1,1,1,3,3-pentafluorbutane, and trans-1,2-dichloroethylene: 33%/28%/39%), both available from MicroCare Corporation.

The residual processing plasticizer content of microporous material according to the present invention is usually less than 10 percent by weight, based on the total weight of the microporous material, and this amount may be further reduced by additional extractions using the same or a different organic extraction liquid. Often the residual processing plasticizer content is less than 5 percent by weight, based on the total weight of the microporous material, and this amount may be further reduced by additional extractions.

The microporous material of the present invention may also be produced according to the general principles and procedures of U.S. Pat. Nos. 2,772,322; 3,696,061; and/or 3,862,030. These principles and procedures are particularly applicable where the polymer of the matrix is or is predominately poly(vinyl chloride) or a copolymer containing a large proportion of polymerized vinyl chloride.

Microporous materials produced by the above-described processes optionally may be stretched. Stretching of the microporous material typically results in both an increase in the void volume of the material, and the formation of regions of increased or enhanced molecular orientation. As is known in the art, many of the physical properties of molecularly oriented thermoplastic organic polymer, including tensile strength, tensile modulus, Young's modulus, and others, differ, e.g., considerably, from those of the corresponding thermoplastic organic polymer having little or no molecular orientation. Stretching is typically accomplished after substantial removal of the processing plasticizer as described above.

Various types of stretching apparatus and processes are well known to those of ordinary skill in the art, and may be used to accomplish stretching of the microporous material of the present invention. Stretching of the microporous materials is described in further detail in U.S. Pat. No. 5,326,391 at column 11, line 45 through column 13, line 13, which disclosure is incorporated herein by reference.

The present invention is more particularly described in the examples that follow, which are intended to be illustrative only, since numerous modifications and variations therein will be apparent to those skilled in the art. Unless otherwise specified, all parts and percentages are by weight.

EXAMPLES

In Part 1 of the following examples, the materials and methods used to prepare the Example and Comparative mixes prepared in the pilot plant and presented in Table 1 and the Example mixes prepared in the scale-up process and Comparative commercial samples presented in Table 2 are described. In Part 2, the methods used to extrude, calender and extract the sheets prepared from the mixes of Part 1 and Part 2 are described. In Part 3, the methods used to determine the physical properties reported in Tables 3 and 4 are described. In Parts 4A and 4B, the coating formulations used are listed in Tables 5 and 7 and the properties of the coated sheets are listed in Tables 6 and 8. In Part 5, The Benzyl Acetate Test results for the products of Tables 1, 2, 6 and 8 are listed in Tables 9, 10, 11 and 12.

Part 1—Mix Preparation

The dry ingredients were weighed into a FM-130D Littleford plough blade mixer with one high intensity chopper style mixing blade in the order and amounts (grams (g)) specified in Table 1. The dry ingredients were premixed for 15 seconds using the plough blades only. The process oil (Mix Oil) was then pumped in via a hand pump through a spray nozzle at the top of the mixer, with only the plough blades running. The pumping time for the examples varied between 45-60 seconds. The high intensity chopper blade was turned on, along with the plough blades, and the mix was mixed for 30 seconds. The mixer was shut off and the internal sides of the mixer were scrapped down to insure all ingredients were evenly mixed. The mixer was turned back on with both high intensity chopper and plough blades turned on, and the mix was mixed for an additional 30 seconds. The mixer was turned off and the mix dumped into a storage container.

TABLE 1

| Samples | Ex. 1 | Ex. 2 | Ex. 3 | Ex. 4 | Ex. 5 | Ex. 6 | Ex. 7 | Ex. 8 | Ex. 11 | CE 1 | CE 2 | CE 3 | CE 4 | CE 5 |
|---|---|---|---|---|---|---|---|---|---|---|---|---|---|---|
| Silica HiSil 135 (a) | 1393 | 1393 | 1393 | 1393 | 0 | 0 | 1814 | 1814 | 1814 | 1393 | 1393 | 2270 | 2270 | 2270 |
| Ca Silicate (b) | 0.0 | 0.0 | 0.0 | 0.0 | 1816 | 1816 | 0.0 | 0.0 | 0.0 | 0.0 | 0.0 | 0.0 | 0.0 | 0.0 |
| CaCO₃ (c) | 544.3 | 544.3 | 544.3 | 544.3 | 709.0 | 709.0 | 0.0 | 0.0 | 0.0 | 544.3 | 544.3 | 0.0 | 0.0 | 0.0 |

TABLE 1-continued

| Samples | Ex. 1 | Ex. 2 | Ex. 3 | Ex. 4 | Ex. 5 | Ex. 6 | Ex. 7 | Ex. 8 | Ex. 11 | CE 1 | CE 2 | CE 3 | CE 4 | CE 5 |
|---|---|---|---|---|---|---|---|---|---|---|---|---|---|---|
| TiO$_2$ (d) | 90.7 | 90.7 | 90.7 | 90.7 | 118.0 | 118.0 | 87.3 | 87.3 | 87.3 | 90.7 | 90.7 | 91.0 | 91.0 | 91.0 |
| UHMWPE (e) | 515.3 | 515.3 | 515.3 | 515.3 | 581.0 | 671.0 | 592.0 | 592.0 | 592.0 | 515.3 | 515.3 | 560.0 | 285.0 | 654.0 |
| HDPE (f) | 475.4 | 475.4 | 475.4 | 475.4 | 710.0 | 619.0 | 129.0 | 0.0 | 0.0 | 475.4 | 475.4 | 560.0 | 654.0 | 654.0 |
| LDPE (g) | 0.0 | 0.0 | 0.0 | 0.0 | 0.0 | 0.0 | 664.5 | 793.5 | 793.5 | 0.0 | 0.0 | 0.0 | 0.0 | 0.0 |
| Antioxidant (h) | 14.5 | 14.5 | 14.5 | 14.5 | 18.9 | 18.9 | 20.1 | 20.1 | 20.1 | 14.5 | 14.5 | 7.7 | 7.7 | 7.7 |
| Lubricant (i) | 14.5 | 14.5 | 14.5 | 14.5 | 18.9 | 18.9 | 21.6 | 21.6 | 21.6 | 14.5 | 14.5 | 22.7 | 22.7 | 22.7 |
| Polypropylene (j) | 0.0 | 0.0 | 0.0 | 0.0 | 0.0 | 0.0 | 0.0 | 0.0 | 0.0 | 0.0 | 0.0 | 185.0 | 370.0 | 0.0 |
| CFA (k) | 0.0 | 0.0 | 0.0 | 0.0 | 0.0 | 0.0 | 0.0 | 0.0 | 0.0 | 0.0 | 0.0 | 0.0 | 0.0 | 194.7 |
| Nanoclay MB (l) | 0.0 | 0.0 | 0.0 | 0.0 | 0.0 | 0.0 | 0.0 | 0.0 | 0.0 | 0.0 | 0.0 | 0.0 | 0.0 | 194.7 |
| Mix oil (m) | 2841 | 2841 | 2841 | 2841 | 931 | 885 | 2836 | 2836 | 2836 | 2841 | 2841 | 3655 | 3851 | 3850 |
| Process Oil (%) | 47.8% | 48.0% | 49.8% | 52.6% | 47.8% | 47.2% | 53.3% | 56.0% | 52.4% | 55.9% | 57.4% | 60.5% | 59.6% | 57.7% |

(a) HI-SIL ® 135 precipitated silica from PPG Industries, Inc.
(b) INHIBISIL75 precipitated calcium silicate from PPG Industries, Inc.
(c) Calcium carbonate from Camel White
(d) TIPURE ® R-103 titanium dioxide from E. I. du Pont de Nemours and Company
(e) GUR ® 4130 Ultra High Molecular Weight Polyethylene (UHMWPE), from Ticona Corp.
(f) FINA ® 1288 High Density Polyethylene (HDPE), from Total Petrochemicals
(g) Petrothene ® NA206000 LDPE from Lyondell Basel
(h) CYANOX ® 1790 antioxidant from Cytec Industries, Inc.
(i) Calcium stearate lubricant, technical grade
(j) Used was PRO-FAX ® 7523 Polypropylene Copolymer from Ashland Distribution.
(k) Foam PE MB, a chemical foaming agent from Amacet Corporation
(l) NanoMax ® HDPE materbatch nanoclay from Nanocor
(m) Tufflo ® 6056 process oil from PPC Lubricants Scale-up Examples 10-18 were prepared in a plant scale-up batch size using production scale equipment similar to the equipment and procedures described above. The scale-up samples were prepared from a mix of ingredients listed in Table 2 as the weight percent of the total mix.

TABLE 2

| Ingredients | Ex. 10 | Ex. 11 | Ex. 12 | Ex 13 | Ex. 14 | Ex. 15 | Ex. 16 | Ex. 17 | Ex. 18 |
|---|---|---|---|---|---|---|---|---|---|
| HiSil ® 135 (a) | 23.66 | 23.66 | 23.66 | 23.66 | 24.77 | 24.77 | 24.77 | 24.77 | 24.77 |
| CaCO$_3$ (c) | 9.24 | 9.24 | 9.24 | 9.24 | 9.68 | 9.68 | 9.68 | 9.68 | 9.68 |
| TiO$_2$ (d) | 1.54 | 1.54 | 1.54 | 1.54 | 1.61 | 1.61 | 1.61 | 1.61 | 1.61 |
| UHMWPE (e) | 8.75 | 8.75 | 8.75 | 8.75 | 9.16 | 9.16 | 9.16 | 8.45 | 8.45 |
| HDPE (f) | 8.07 | 8.07 | 8.07 | 8.07 | 8.45 | 8.45 | 8.45 | 9.16 | 9.16 |
| Antioxidant (h) | 0.25 | 0.25 | 0.25 | 0.25 | 0.26 | 0.26 | 0.26 | 0.26 | 0.26 |
| Lubricant (i) | 0.25 | 0.25 | 0.25 | 0.25 | 0.26 | 0.26 | 0.26 | 0.26 | 0.26 |
| Mix Oil (m) | 48.24 | 48.24 | 48.24 | 48.24 | 45.81 | 45.81 | 45.81 | 45.81 | 45.81 |

Part 2—Extrusion, Calendering and Extraction

The mixes of the Examples 1-9 and Comparative Examples 1-5 were extruded and calendered into final sheet form using an extrusion system including a feeding, extrusion and calendering system described as follows. A gravimetric loss in weight feed system (K-tron model #K2MLT35D5) was used to feed each of the respective mixes into a 27 mm twin screw extruder (model # was Leistritz Micro-27gg). The extruder barrel was comprised of eight temperature zones and a heated adaptor to the sheet die. The extrusion mixture feed port was located just prior to the first temperature zone. An atmospheric vent was located in the third temperature zone. A vacuum vent was located in the seventh temperature zone.

The mix was fed into the extruder at a rate of 90 g/minute. Various amounts of additional processing oil also was injected at the first temperature zone, as required, to achieve the desired total oil content in the extruded sheet. The oil contained in the extruded sheet (extrudate) being discharged from the extruder is referenced herein as the "extrudate oil" or "process oil", and is reported in weight percent in Table 1, based on the total weight of the extruded sheet. In accordance with an embodiment of the present invention, densities of greater than 0.8 g/cm$^3$ of the microporous sheet are obtained when the amount of process oil (extrudate oil) in the extruded sheet is less than 57 weight percent. While not wishing to be bound by any particular theory, it is believed from the experimental evidence at hand that lowering the amount of process oil in the extruded microporous sheet increases the density of the microporous sheet, e.g., to greater than 0.8 g/cm$^3$ and alters the surface of the sheet so that volatile material transferred to the vapor release surface is more dispersed and does not pool initially into droplets on that surface.

Extrudate from the barrel was discharged into a 15-centimeter wide sheet Masterflex® die having a 1.5 millimeter discharge opening. The extrusion melt temperature was 203-210° C. and the throughput was 7.5 kilograms per hour.

The calendering process was accomplished using a three-roll vertical calender stack with one nip point and one cooling roll. Each of the rolls had a chrome surface. Roll dimensions were approximately 41 cm in length and 14 cm in diameter. The top roll temperature was maintained between 135° C. to 140° C. The middle roll temperature was maintained between 140° C. to 145° C. The bottom roll was a cooling roll wherein the temperature was maintained between 10-21° C. The extrudate was calendered into sheet form and passed over the bottom water cooled roll and wound up.

A sample of sheet cut to a width up to 25.4 cm and length of 305 cm was rolled up and placed in a canister and exposed to hot liquid 1,1,2-trichloroethylene for approximately 7-8 hours to extract oil from the sheet sample. Afterwards, the extracted sheet was air dried and subjected to test methods described hereinafter.

The mixes of the Scale-up Examples 10-18, as shown in Table 2, were extruded and calendered into final sheet form using an extrusion system and oil extraction process that was a production sized version of the system described above, carried out as described in U.S. Pat. No. 5,196,262, at column 7, line 52, to column 8, line 47, which description is incorporated herein by reference. The final sheets were tested for physical parameters using the test methods described above in Part 3. Comparative Examples 6-10 were commercial microporous products identified as follows: CE 6 was TESLIN® Digital 10 mil; CE 7 was Teslin® SP 6 mil; CE 8 was TESLIN® SP 10 mil; CE 9 was TESLIN® SP 14 mil; and CE 10 was TESLIN® SP 12 mil.

The extrudate oil (weight percent) for the commercial products used for comparative examples 6-10 varied from 57 to 62 percent.

Part 3—Testing and Results

Physical properties measured on the extracted and dried films and the results obtained are listed in Tables 3 and 4. The extrudate oil weight percent was measured using a Soxhlet extractor. The extrudate oil weight percent determination used a specimen of extrudate sheet with no prior extraction. A sample specimen approximately 2.25 inches×5 inches (5.72 cm×12.7 cm) was weighed and recorded to four decimal places. Each specimen was then rolled into a cylinder and placed into a Soxhlet extraction apparatus and extracted for approximately 30 minutes using trichloroethylene (TCE) as the solvent. The specimens were then removed and dried. The extracted and dried specimens were then weighed. The oil weight percentage values (extrudate) were calculated as follows: Oil Wt. %=(initial wt.−extracted wt.)×100/initial wt.

Thickness was determined using an Ono Sokki thickness gauge EG-225. Two 4.5 inches×5 inch (11.43 cm×12.7 cm) specimens were cut from each sample and the thickness for each specimen was measured in nine places (at least ¾ of an inch (1.91 cm) from any edge). The arithmetic average of the readings was recorded in mils to 2 decimal places and converted to microns.

The density of the above-described examples was determined by dividing the average anhydrous weight of two specimens measuring 4.5 inches×5 inches (11.43 cm×12.7 cm) that were cut from each sample by the average volume of those specimens. The average volume was determined by boiling the two specimens in deionized water for 10 minutes, removing and placing the two specimens in room temperature deionized water, weighing each specimen suspended in deionized water after it has equilibrated to room temperature and weighing each specimen again in air after the surface water was blotted off. The average volume of the specimens was calculated as follows:

Volume (avg.)=[(weight of lightly blotted specimens weighed in air−sum of immersed weights)× 1.002]/2

The anhydrous weight was determined by weighing each of the two specimens on an analytical balance and multiplying that weight by 0.98 since it was assumed that the specimens contained 2 percent moisture.

The Porosity reported in Tables 3 and 4 was determined using a Gurley densometer, model 4340, manufactured by GPI Gurley Precision Instruments of Troy, N.Y. The Porosity reported was a measure of the rate of air flow through a sample or it's resistance to an air flow through the sample. The unit of measure is a "Gurley second" and represents the time in seconds to pass 100 cc of air through a 1 inch square ($6.4 \times 10^{-4}$ m$^2$) area using a pressure differential of 4.88 inches of water ($12.2 \times 10^2$ Pa). Lower values equate to less air flow resistance (more air is allowed to pass freely). The measurements were completed using the procedure listed in the manual, *MODEL* 4340 *Automatic Densometer and Smoothness Tester Instruction Manual*. TAPPI method T 460 om-06-Air Resistance of Paper can also be referenced for the basic principles of the measurement.

TABLE 3

| Property | Ex. 1 | Ex. 2 | Ex. 3 | Ex. 4 | Ex. 5 | Ex. 6 | Ex. 7 | Ex. 8 | Ex. 9 | CE 1 | CE 2 | CE 3 | CE 4 | CE 5 |
|---|---|---|---|---|---|---|---|---|---|---|---|---|---|---|
| Sheet Thickness (μm) | 262 | 264 | 264 | 262 | 371 | 419 | 173 | 155 | 173 | 260 | 246 | 174 | 160 | 169 |
| Extrudate Oil wt. % | 47.8% | 48.0% | 49.8% | 52.6% | 47.8% | 47.2% | 53.5% | 56.0% | 52.4% | 55.9% | 57.4% | 60.5% | 59.6% | 57.7% |
| Density (g/cc) | 0.764 | 0.828 | 0.755 | 0.707 | 0.892 | 0.901 | 0.646 | 0.612 | 0.701 | 0.750 | 0.695 | 0.584 | 0.659 | 0.620 |
| Porosity (Gurley Sec.) | 2148 | 2161 | 2009 | 1988 | 1685 | 1730 | 3787 | 3735 | 4155 | 1842 | 1517 | 1473 | 1309 | 1410 |

TABLE 4

| Property | Ex. 10 | Ex. 11 | Ex. 12 | Ex. 13 | Ex. 14 | Ex. 15 | Ex. 16 | Ex. 17 | Ex. 18 | GE 6 | CE 7 | CE 8 | CE 9 | CE 10 |
|---|---|---|---|---|---|---|---|---|---|---|---|---|---|---|
| Sheet Thickness (μm) | 291 | 293 | 269 | 286 | 289 | 288 | 278 | 277 | 284 | 284 | 157 | 250 | 359 | 306 |
| Extrudate Oil wt. % | 58.0% | 57.6% | 58.0% | 57.1% | 55.0% | 53.5% | 54.0% | 54.0% | 53.0% | — | — | — | — | — |
| Density (g/cc) | 0.795 | 0.804 | 0.809 | 0.815 | 0.818 | 0.882 | 0.835 | 0.835 | 0.862 | 0.719 | 0.607 | 0.677 | 0.691 | 0.672 |

TABLE 4-continued

| Property | Ex. 10 | Ex. 11 | Ex. 12 | Ex. 13 | Ex. 14 | Ex. 15 | Ex. 16 | Ex. 17 | Ex. 18 | GE 6 | CE 7 | CE 8 | CE 9 | CE 10 |
|---|---|---|---|---|---|---|---|---|---|---|---|---|---|---|
| Porosity (Gurley Sec.) | 2877 | 3017 | 3395 | 3208 | 2800 | 2872 | 3048 | 2849 | 3102 | 5983 | 1867 | 3659 | 4110 | 4452 |

Part 4 A—Coating Formulations and Coated Products

Coatings 1-5 listed in Table 5 were prepared by dispersing CELVOL® 325 polyvinyl alcohol in cool water under mild agitation in a 600 mL beaker. Mild agitation was provided with a 1" (2.54 cm) paddle stirrer driven by an electric stir motor. The mixture was heated to 190° F. (87.8° C.) and stirred for 20-30 minutes. The resultant solution was allowed to cool to room temperature while stirring. Specific mix amounts and resultant measured solids are outlined in Table 5.

TABLE 5

Coating Formulations

| Coating # | CELVOL ® 325, (grams) | Deionized water, (grams) | Measured Solids, % by weight |
|---|---|---|---|
| 1 | 7.5 | 292.5 | 2.5 ± 0.3 |
| 2 | 11.3 | 288.7 | 3.8 ± 0.3 |
| 3 | 13.5 | 286.5 | 4.5 ± 0.3 |
| 4 | 18.0 | 282.0 | 6.0 ± 0.3 |
| 5 | 15.0 | 285.0 | 5.0 ± 0.3 |

The coatings, confirmed to be free of visible undissolved particles, were applied to TESLIN® HD microporous substrate sold by PPG Industries, Pittsburgh, Pa. The coatings were applied to sheets of 8.5 inches×11 inches, (21.59 cm×27.94 cm) 11 mils thick substrate each of which had been tare on a balance prior to placing the sheet on a clean glass surface and using tape to adhere the top corners of the sheet to the glass. A piece of clear 10 mil thick polyester 11 inches×3 inches (27.94 cm×7.62 cm) was positioned across the top edge of the sheet, covering ½ inch (1.27 cm) down from the top edge of the sheet. The polyester was fixed to the glass surface with tape. A wire wrapped metering rod from Diversified Enterprises was placed 1-2 inches (2.5-5.1 cm) above the sheet, parallel to the top edge, near the top edge of the polyester. A 10-20 mL quantity of coating was deposited as a bead strip (approximately ¼ inch (0.64 cm) wide) directly next to and touching the metering rod using a disposable pipette. The bar was drawn completely across the sheet, attempting a continuous/constant rate. The resultant wet sheet was removed from the glass surface, immediately placed on the previously tare balance, weighed, the wet coating weight recorded then the coated sheet was placed in a forced air oven and dried at 95° C. for 2 minutes. The dried sheet was removed from the oven and the same coating procedure was repeated to the same coated sheet surface. The two wet coating weights were used to calculate the final dry coat weight in grams per square meter. The coated sheets of Examples 19-23 are described in Table 6.

TABLE 6

Final Coated Sheets

| Example # | Coating Solids, % | Wire Wrapped Rod # | $1^{st}$ Wet Coat Weight, grams | $2^{nd}$ Wet Coat Weight, grams | Total wet coating weight, grams | Calculated Final Coat Weight, gsm |
|---|---|---|---|---|---|---|
| 19 | 2.5 | 3 | 0.6 | 0.65 | 1.25 | 0.5 ± 0.1 |
| 20 | 3.8 | 3 | 0.61 | 0.59 | 1.20 | 0.75 ± 0.1 |
| 21 | 4.5 | 3 | 0.70 | 0.64 | 1.34 | 1.0 ± 0.2 |
| 22 | 6 | 3 | 0.76 | 0.64 | 1.40 | 1.5 ± 0.1 |
| 23 | 5 | 10 | 1.18 | 1.20 | 2.38 | 2.1 ± 0.2 |

The following formula was used to calculate the final dry coat weight.

Calculated Final Dry Coat Weight in grams per square meter=((coatings solids×0.01)×($1^{st}$ wet coating wgt.+$2^{nd}$ wet coating wgt.))/(8.5×10.5)×1550

Part 4B—Coating Formulations and Coated Products

The procedure of Part 4A was followed in preparing the coating formulations of Coatings 6-12, except that Coating 7 was mixed for 2 days prior to use. The coating formulations are listed in Table 7.

The substrate used in this Part 4B was TESLIN® SPI000 microporous substrate sold by PPG Industries, Pittsburgh, Pa. The same procedure used in Part 4A was followed except that some sheets were coated on both sides, drying the first coated side prior to applying the second on the opposite side and a number 9 metering rod was used for all of the coatings. Information on the final coated sheets is included in Table 8.

TABLE 7

Coating Formulations with amounts listed in grams

| Ingredients | 6 | 7 | 8 | 9 | 10 | 11 | 12 |
|---|---|---|---|---|---|---|---|
| Witcobond W240$_{(n)}$ | 8 | 8 | 8 | 8 | 16 | 0 | 0 |
| Aerosil ® 200$_{(o)}$ | 2.5 | 0 | 0 | 0 | 0 | 0 | 0 |
| CaCO$_{3(c)}$ | 0 | 2.5 | 0 | 0 | 0 | 0 | 0 |
| HiSil ® T 700$_{(p)}$ | 0 | 0 | 2.5 | 0 | 0 | 0 | 0 |
| Lo-Vel ® 6200$_{(q)}$ | 0 | 0 | 0 | 2.5 | 0 | 0 | 0 |
| MOMENTIVE LE-410$_{(r)}$ | 0 | 0 | 0 | 0 | 0 | 0.54 | 0 |
| HYCAR 26138$_{(s)}$ | 0 | 0 | 0 | 0 | 0 | 0 | 10 |
| Deionized Water | 39.5 | 39.5 | 39.5 | 39.5 | 34.0 | 49.5 | 40 |
| Total, grams | 50 | 50 | 50 | 50 | 50 | 50 | 50 |
| Solids, % | 10 | 10 | 10 | 10 | 10 | 0.4 | 10 |

$_{(n)}$WITCOBOND W-240, an aqueous polyurethane dispersion from Chemtura Corporation.
$_{(o)}$Aerosil ® 200 fumed silica from Degussa.
$_{(p)}$HiSil ® T700 precipitated silica from PPG Industries, Inc.
$_{(q)}$Lo-Vel ® 6200 precipitated silica from PPG Industries, Inc.
$_{(r)}$MOMENTIVE LE-410 an aqueous silicon dispersion from Momentive Performance Materials.
$_{(s)}$HYCAR 26138, an aqueous poly(meth)acrylate dispersion from Lubrizol Advanced Materials, Inc.

TABLE 8

Final Coated Sheets

| Example # | Coating # | Coating Type | Wet Coating weight (grams) | Final Coating weight (gsm) |
|---|---|---|---|---|
| 24 | 10 | Single | 0.95 | 1.7 |
| 25 | 10 | Both Sides | 2.0 | 3.5 |
| 26 | 11 | Both Sides | 2.0 | 0.14 |
| 27 | 12 | Both Sides | 2.1 | 3.9 |
| CE 11 | 11 | Single | 0.9 | 0.07 |
| CE 12 | 12 | Single | 1.1 | 1.9 |
| CE 13 | 6 | Both Sides | 2.2 | 3.8 |
| CE 14 | 7 | Both Sides | 2.5 | 4.4 |
| CE 15 | 8 | Both Sides | 2.3 | 3.9 |
| CE 16 | 9 | Both Sides | 2.3 | 4.0 |

Part 5—Benzyl Acetate Testing

The holder assembly used for evaporation rate and performance testing of a membrane consisted of a front clamp with a ring gasket, a back clamp, test reservoir cup and four screws. The test reservoir cup was fabricated from a clear thermoplastic polymer, having interior dimensions defined by a circular diameter at the edge of the open face of approximately 4 centimeters and a depth of no greater than 1 centimeter. The open face was used to determine the volatile material transfer rate.

Each clamp of the holder assembly had a 1.5 inch (3.8 cm) diameter circular opening to accommodate the test reservoir cup and provide an opening to expose the membrane under test. When placing a membrane under test, i.e., a sheet of microporous material having a thickness of from 6 to 18 mils, the back clamp of the holder assembly was placed on top of a cork ring. The test reservoir cup was placed in the back clamp and charged with approximately 2 mL of benzyl acetate. An approximately 2 inch (5.1 cm) diameter disk was cut out of the membrane sheet and placed directly over and in contact with the edge of the reservoir cup such that 12.5 $cm^2$ of the volatile material contact surface of the microporous sheet was exposed to the interior of the reservoir.

The front clamp of the holder was carefully placed over the entire assembly, with the screw holes aligned and so as not to disturb the membrane disk. When a coated microporous sheet was used, the coated surface was placed either toward the reservoir or toward the atmosphere as indicated in the Table below. The screws were attached and tightened enough to prevent leaking. The ring gasket created a seal. The holder was labeled to identify the membrane sample under test. From 5 to 10 replicates were prepared for each test. Five replicates of a Control (uncoated sample) was included for the coated Examples. For the Examples in Table 11, there were 5 Controls for each Example and the average evaporation rate for each Control was reported with the corresponding Example as well as the percent reduction in evaporation rate of the example compared to the corresponding Control. The coated surface of Example 19-23 in Table 11 was towards the atmosphere.

Each holder assembly was weighed to obtain an initial weight of the entire charged assembly. The assembly was then placed, standing upright, in a laboratory chemical fume hood having approximate dimensions of 5 feet [1.52 meters] (height)×5 feet [1.52 meters](width)×2 feet [0.61 meters] (depth). With the test reservoir standing upright, benzyl acetate was in direct contact with at least a portion of the volatile material contact surface of the microporous sheet. The glass doors of the fume hood were pulled down, and the air flow through the hood was adjusted so as to have eight (8) turns (or turnovers) of hood volume per hour. Unless otherwise indicated, the temperature in the hood was maintained at 25° C.±5° C. The humidity within in the fume hood was ambient. The test reservoirs were regularly weighed in the hood. Testing was performed for five (5) days. The calculated weight loss of benzyl acetate, in combination with the elapsed time and surface area of the microporous sheet exposed to the interior of the test reservoir, were used to determine the volatile material transfer rate of the microporous sheet, in units of mg/(hour*$cm^2$). The average evaporation rate (mg/hr) of the replicates was reported for the entire assembly in the Tables below. These two values are related by the following formula:

Average evaporation rate (mg/hr)/12.5 $cm^2$=Volatile Material transfer rate (mg/hour*$cm^2$)

Marginal (Marg.) indicates that there were both passing and failing replicates, or that the test had no failures as described by "pooling" and "dripping" of the benzyl acetate down the surface of the membrane, but had some drops of benzyl acetate forming beads on the surface of the membrane, which was also deemed unacceptable vis-à-vis, to be graded as a "pass" result. There is, however, a clear performance distinction between a failing (FAIL) test result and a marginal (Marg.) test result, the latter being clearly superior, as discussed herein.

The date of Tables 2, 4 and 10 for Examples 10-18 and Comparative Examples 6-10, which illustrate microporous sheets produced on production scale equipment, confirm the correlation between increased sheet density, which is achieved by lowering the amount of extrudate oil in the extruded sheet, and passing of the benzyl acetate test. This data is summarized in Table 13.

TABLE 9

| Samples | Ex. 1 | Ex. 2 | Ex. 3 | Ex. 4 | Ex. 5 | Ex. 6 | Ex. 7 | Ex. 8 | Ex. 9 | CE 1 | CE 2 | CE 3 | CE 4 | CE 5 |
|---|---|---|---|---|---|---|---|---|---|---|---|---|---|---|
| 5 Day Results | Pass | Pass | Pass | Pass | Pass | Pass | Pass | Pass | Pass | Fail | Fail | Fail | Fail | Fail |
| Evaporation rate | 2.8 | 2.8 | 2.6 | 2.8 | 2.7 | 4.3 | 3.2 | 3.3 | 3.2 | 3.0 | 3.1 | 2.9 | 2.6 | 2.8 |

TABLE 10

| Samples | Ex. 10 | Ex. 11 | Ex. 12 | Ex. 13 | Ex. 14 | Ex. 15 | Ex. 16 | Ex. 17 | Ex. 18 | CE 6 | CE 7 | CE 8 | CE 9 | CE 10 |
|---|---|---|---|---|---|---|---|---|---|---|---|---|---|---|
| 5 Day Results | Marg. | Marg. | Marg. | Marg. | Pass | Pass | Pass | Pass | Pass | Fail | Fail | Fail | Fail | Fail |
| Evaporation Rate | 3.4 | 3.3 | 3.2 | 3.2 | 3.7 | 3.9 | 3.7 | 3.8 | 3.7 | 2.9 | 3.0 | 3.0 | 3.3 | 3.1 |

TABLE 11

| Samples | Ex. 19 | Control | Ex. 20 | Control | Ex. 21 | Control | Ex. 22 | Control | Ex. 23 | Control |
|---|---|---|---|---|---|---|---|---|---|---|
| 5 Day Results | Pass | Fail | Pass | Fail | Pass | Fail | Pass | Fail | Pass | Fail |
| Evaporation rate | 4.09 | 4.65 | 3.61 | 4.69 | 2.05 | 4.10 | 2.68 | 4.69 | 1.25 | 4.03 |
| Percent Reduction in Evaporation Rate | 12 | | 23 | | 50 | | 46 | | 69 | |

TABLE 12

| Samples | Control [1] | Ex. 24 Ctr [2] | Ex. 24 Cta [3] | Ex. 25 | Control [4] | Ex. 26 | Ex. 27 | CE 11 Cta [3] | CE 12 Cta [3] | CE 13 | CE 14 | CE 15 | CE 16 |
|---|---|---|---|---|---|---|---|---|---|---|---|---|---|
| 5 Day Results | Fail | Pass | Pass | Pass | Fail | Pass | Pass | Fail | Fail | Fail | Fail | Fail | Fail |
| Evaporation Rate | 2.64 | 2.64 | 2.61 | 2.83 | 3.4 | 3.3 | 3.4 | 3.3 | 3.2 | 2.64 | 2.63 | 2.56 | 2.65 |

[1] Control of uncoated TESLIN ® HD microporous material that was included with Examples 24, 25, CE 13-16.
[2] Coated surface was directed toward reservoir of volatile material.
[3] Coated surface was directed toward the atmosphere.
[4] Control of uncoated TESLIN ® HD microporous material that was included with Examples 26, 27, CE 11-12.

TABLE 13

| Example Set | Benzyl Acetate Test Result | Sheet Density, g/cc | Extrudate Oil, weight % |
|---|---|---|---|
| Ex. 14-18 | Pass | 0.818-0.882 | 53-55 |
| Ex. 10-13 | Marginal | 0.795-0.815 | 57-58 |
| CE 6-10 | Fail | 0.607-0.719 | 57-62 |

Whereas particular embodiments of this invention have been described above for purposes of illustration, it will be evident to those skilled in the art that numerous variations of the details of the present invention may be made without departing from the invention as defined in the appended claims.

What is claimed is:

1. A vapor permeable microporous material in contact with a volatile material, the microporous material comprising:
   (a) a matrix of substantially water-insoluble thermoplastic organic polymer comprising polyolefin, wherein the polyolefin comprises a mixture of substantially linear ultrahigh molecular weight polyethylene and lower molecular weight polyethylene comprising high density polyethylene, wherein said substantially linear ultrahigh molecular weight polyethylene constitutes at least one percent by weight of said matrix and said substantially linear ultrahigh molecular weight polyethylene and said lower molecular weight polyethylene together constitute substantially 100 percent by weight of the polymer of the matrix;
   (b) finely divided, substantially water-insoluble particulate filler comprising particulate precipitated silica having a BET surface area ranging from 25 to 350 square meters per gram, said particulate filler being distributed throughout said matrix and constituting from 40 to 90 percent by weight, based on the total weight of said microporous material; and
   (c) a network of interconnecting pores communicating substantially throughout said microporous material, wherein said pores have a volume average diameter ranging from 0.02 to 0.50 micrometers;
   wherein said microporous material has:
   (1) a density of at least 0.8 g/cm$^3$,
   (2) a volatile material contact surface and a vapor release surface, said volatile material contact surface and said vapor release surface being substantially opposed to each other, and
   (3) a volatile material transfer rate from said volatile material contact surface to said vapor release surface of from 0.04 to 0.6 mg/(hour*cm$^2$) when the volatile material contact surface of the vapor permeable microporous material is placed in contact with a volatile material and said vapor release surface is not in direct contact with the volatile material, the density of the microporous material being such that when volatile material is transferred from said volatile material contact surface to said vapor release surface, said vapor release surface is substantially free of liquid volatile material in liquid form.

2. The microporous material of claim 1 wherein said microporous material has a density of from 0.8 to 1.2 g/cm$^3$.

3. The microporous material of claim 1 wherein said volatile material transfer rate is from 0.30 to 0.55 mg/(hour*cm$^2$).

4. The microporous material of claim 1 wherein said volatile material transfer rate is from 0.35 to 0.50 mg/(hour*cm$^2$).

5. The microporous material of claim 1 wherein said volatile material contact surface and said vapor release surface are each free of a coating material.

6. The microporous material of claim 1 wherein at least a portion of said volatile material contact surface has a first coating thereon, and/or at least a portion of said vapor release surface has a second coating thereon.

7. The microporous material of claim 6 wherein said first coating and said second coating each independently is formed from an aqueous coating composition selected from the group consisting of aqueous poly(meth)acrylate dispersions, aqueous polyurethane dispersions, and combinations thereof.

8. The microporous material of claim 7 wherein each aqueous coating composition comprises a dispersion of particles having a particle size of from 200 to 400 nm.

9. The microporous material of claim 8 wherein said first coating and said second coating each independently have a coating weight of from 0.01 to 5.5 g/m$^2$.

10. The microporous material of claim 1 wherein said polyolefin of the water-insoluble thermoplastic organic polymer comprises ultrahigh molecular weight polyethylene having an intrinsic viscosity of at least 10 deciliters/gram.

11. The microporous material of claim 10 wherein said ultrahigh molecular weight polyolefin is ultrahigh molecular weight polyethylene having an intrinsic viscosity of at least 18 deciliters/gram.

12. The microporous material of claim 1 wherein said substantially linear ultrahigh molecular weight polyethylene has an intrinsic viscosity of at least 10 deciliters/gram and said lower molecular weight polyethylene has an ASTM D 1238-86 Condition E melt index of less than 50 grams/10 minutes and an ASTM D 1238-86 Condition F melt index of at least 0.1 grams/10 minutes.

13. The microporous material of claim 1 wherein said pores constitute from 35 to 95 percent by volume of said microporous material, based on the total volume of said microporous material.

14. A vapor permeable microporous material in contact with a volatile material, the microporous material comprising:
(a) a matrix of substantially water-insoluble thermoplastic organic polymer comprising polyolefin comprising a mixture of substantially linear ultrahigh molecular weight polyethylene and lower molecular weight polyethylene comprising high density polyethylene, wherein said substantially linear ultrahigh molecular weight polyethylene constitutes at least one percent by weight of said matrix and said substantially linear ultrahigh molecular weight polyethylene and said lower molecular weight polyethylene together constitute substantially 100 percent by weight of the polymer of the matrix, and wherein the substantially linear ultrahigh molecular weight polyethylene has an intrinsic viscosity of at least 10 deciliters/gram;
(b) finely-divided, substantially water-insoluble particulate silica having a BET surface area ranging from 25 to 350 square meters per gram, said particulate silica being distributed throughout said matrix and constituting from 40 to 90 percent by weight, based on the total weight of said microporous material; and
(c) a network of interconnecting pores communicating substantially throughout said microporous material, said pores having a volume average diameter ranging from 0.02 to 0.50 micrometers and constituting from 35 to 95 percent by volume of said microporous material, based on the total volume of said microporous material;
wherein said microporous material has:
(1) a density of from 0.8 to 1.2 g/cm$^3$,
(2) a volatile material contact surface and a vapor release surface, said volatile material contact surface and said vapor release surface being substantially opposed to each other, and
(3) a volatile material transfer rate from said volatile material contact surface to said vapor release surface of from 0.04 to 0.6 mg/(hour*cm$^2$), when the volatile material contact surface of the vapor permeable microporous material is placed in contact with a volatile material and said vapor release surface is not in direct contact with the volatile material, the density of the microporous material being such that when volatile material is transferred from said volatile material contact surface to said vapor release surface, said vapor release surface is substantially free of volatile material in liquid form.

15. The vapor permeable microporous material of claim 14 wherein:
(a) the lower molecular weight polyethylene has an ASTM D 1238-86 Condition E melt index of less than 50 grams/10 minutes and an ASTM D 1238-86 Condition F melt index of at least 0.1 grams/10 minutes;
(b) the particulate silica is precipitated silica; and
(c) the volatile material transfer rate of the microporous material is 0.30 to 0.55 mg/(hour*cm$^2$).

16. A vapor permeable microporous material in contact with a volatile material, the microporous material comprising:
(a) a matrix of substantially water-insoluble thermoplastic organic polymer comprising polyolefin, wherein the polyolefin comprises a mixture of substantially linear ultrahigh molecular weight polyethylene and lower molecular weight polyethylene comprising high density polyethylene, wherein said substantially linear ultrahigh molecular weight polyethylene constitutes at least one percent by weight of said matrix and said substantially linear ultrahigh molecular weight polyethylene and said lower molecular weight polyethylene together constitute substantially 100 percent by weight of the polymer of the matrix;
(b) finely divided, substantially water-insoluble particulate filler comprising particulate precipitated silica, said particulate filler being distributed throughout said matrix and constituting from 40 to 90 percent by weight, based on the total weight of said microporous material; and
(c) a network of interconnecting pores communicating substantially throughout said microporous material, wherein said pores have a volume average diameter ranging from 0.02 to 0.50 micrometers;
wherein said microporous material has:
(1) a density of at least 0.8 g/cm$^3$;
(2) a volatile material contact surface and a vapor release surface, said volatile material contact surface and said vapor release surface being substantially opposed to each other; and
(3) a volatile material transfer rate from said volatile material contact surface to said vapor release surface of from 0.04 to 0.6 mg/(hour*cm$^2$) when the volatile material contact surface of the vapor permeable microporous material is placed in contact with a volatile material and said vapor release surface is not in direct contact with the volatile material, the density of the microporous material being such that when volatile material is transferred from said volatile material contact surface to said vapor release surface, said vapor release surface is substantially free of liquid volatile material in liquid form,
wherein at least a portion of said volatile material contact surface has a first coating thereon, and/or at least a portion of said vapor release surface has a second coating thereon, wherein said first coating and said second coating each independently is formed from an aqueous coating composition selected from the group consisting of aqueous poly (meth)acrylate dispersions, aqueous polyurethane dispersions, and combinations thereof.

* * * * *